(12) United States Patent
Garcia et al.

(10) Patent No.: US 11,565,024 B2
(45) Date of Patent: Jan. 31, 2023

(54) LYSOSTAPHIN CONTAINING SYNTHETIC HYDROGEL CARRIERS FOR BONE REPAIR

(71) Applicant: Georgia Tech Research Corporation, Atlanta, GA (US)

(72) Inventors: Andres J. Garcia, Atlanta, GA (US); Christopher Thomas Johnson, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 0 days.

(21) Appl. No.: 16/191,685

(22) Filed: Nov. 15, 2018

(65) Prior Publication Data
US 2019/0192738 A1 Jun. 27, 2019

Related U.S. Application Data

(60) Provisional application No. 62/587,190, filed on Nov. 16, 2017.

(51) Int. Cl.
*A61K 38/10* (2006.01)
*A61K 38/04* (2006.01)
(Continued)

(52) U.S. Cl.
CPC .............. *A61L 27/52* (2013.01); *A61K 38/10* (2013.01); *A61K 38/16* (2013.01); *A61L 27/18* (2013.01); *A61L 27/227* (2013.01); *A61L 27/26* (2013.01); *A61L 27/48* (2013.01); *A61L 27/54* (2013.01); *A61M 5/19* (2013.01); *A61M 5/3294* (2013.01); *A61L 2300/25* (2013.01); *A61L 2300/252* (2013.01); *A61L 2300/404* (2013.01); *A61L 2300/412* (2013.01); *A61L 2300/414* (2013.01); *A61L 2400/06* (2013.01); *A61L 2430/02* (2013.01); *A61M 2202/07* (2013.01); *A61M 2210/02* (2013.01)

(58) Field of Classification Search
None
See application file for complete search history.

(56) References Cited

U.S. PATENT DOCUMENTS

| 2003/0211995 A1 | 11/2003 | Kokai-Kun et al. |
| 2015/0182606 A1 | 7/2015 | Fischer et al. |
| 2017/0145398 A1 | 5/2017 | Griswold et al. |

FOREIGN PATENT DOCUMENTS

| CN | 17444905 | 3/2006 |
| CN | 101618209 | 1/2010 |

(Continued)

OTHER PUBLICATIONS

Reyes, C. D., et al. J. Biomed. Mat. Res. (2003), 65(4); 511-523.*
(Continued)

*Primary Examiner* — Kevin S Orwig
(74) *Attorney, Agent, or Firm* — Meunier Carlin & Curfman LLC

(57) ABSTRACT

Disclosed herein are synthetic hydrogels suitable for delivering antimicrobial proteins, optionally in combination with bone regenerating agents to injured tissues. The hydrogels can include lysostaphin and one or more bone morphogenic proteins. The hydrogels are composed of a network of crosslinked hydrophilic polymers and adhesion peptides.

15 Claims, 26 Drawing Sheets

Specification includes a Sequence Listing.

(51) Int. Cl.
| | |
|---|---|
| A61L 27/52 | (2006.01) |
| A61L 27/18 | (2006.01) |
| A61L 27/26 | (2006.01) |
| A61M 5/19 | (2006.01) |
| A61M 5/32 | (2006.01) |
| A61L 27/54 | (2006.01) |
| A61L 27/48 | (2006.01) |
| A61L 27/22 | (2006.01) |
| A61K 38/16 | (2006.01) |

(56) References Cited

FOREIGN PATENT DOCUMENTS

| | | |
|---|---|---|
| EP | 1671644 | 6/2006 |
| EP | 1885403 | 5/2013 |
| WO | 1999004809 | 2/1999 |
| WO | 2008105826 | 9/2008 |
| WO | 2015100447 | 7/2015 |

OTHER PUBLICATIONS

Mhanna, R., et al. Tissue Eng. (2014), 20; 1165-1174.*
Khew, S. T., et al. Biomacromol. (2007), 8; 3153-3161.*
Phelps, E. A., et al. Adv. Mater. (2012), 24(1); 64-2.*
Cui, F., et al. Drug Delivery (2010), 18(3); 173-180.*
Hathaway, H., et al. J. Control. Release (2017), 245; 108-115.*
Watters, C. M., et al. Infection and Drug Resistance (2016), 9; 71-78.*
Bröker, et al., The T Cell Response to Staphylococcus aureus, Pathogens 5(1) (2016) 31.
Bryers J.D., Medical biofilms. Biotechnology and bioengineering 100, 1-18 (2008).
Dajcs, et al., Immunity to lysostaphin and its therapeutic value for ocular MRSA infections in the rabbit, Investigative ophthalmology & visual science 43(12) (2002) 3712-3716.
Dajcs, et al., Lysostaphin treatment of methicillin-resistant Staphylococcus aureus keratitis in the rabbit, Investigative ophthalmology & visual science 41(6) (2000) 1432-1437.
Desbois, et al., In vivo efficacy of the antimicrobial peptide ranalexin in combination with the endopeptidase lysostaphin against wound and systemic meticillin-resistant Staphylococcus aureus (MRSA) infections, International journal of antimicrobial agents 35(6) (2010) 559-565.
F. Cui, G. Li, J. Huang, J. Zhang, M. Lu, W. Lu, J. Huan, Q. Huang, Development of chitosan-collagen hydrogel incorporated with lysostaphin (CCHL) burn dressing with anti-methicillin-resistant Staphylococcus aureus and promotion wound healing properties, Drug Deliv 18(3) (2011) 173-80.
F. Cui, G. Li, J. Huang, J. Zhang, M. Lu, W. Lu, Q. Huang, Extension of nasal anti-Staphylococcus aureus efficacy of lysostaphin by its incorporation into a chitosan-o/w cream, Drug Deliv 17(8) (2010) 617-23.
Flemming, et al., The biofilm matrix. Nat Rev Microbiol 8, 623-633 (2010).
Garcia, et al., Integrin-specific hydrogels functionalized with VEGF for vascularization and bone regeneration of critical-size bone defects. Journal of biomedical materials research. Part A 104, 889-900 (2016).
Gillaspy, wt al., Role of the accessory gene regulator (agr) in pathogenesis of staphylococcal osteomyelitis. Infection and immunity 63, 3373-3380 (1995).
Gründling, et al., Cross-linked peptidoglycan mediates lysostaphin binding to the cell wall envelope of Staphylococcus aureus, Journal of bacteriology 188(7) (2006) 2463-2472.
Gründling, et al., Staphylococcus aureus mutants with increased lysostaphin resistance. Journal of bacteriology 188, 6286-6297 (2006).
Harmata, et al., d-amino Acid Inhibits Biofilm but not New Bone Formation in an Ovine Model, Clinical Orthopaedics and Related Research® 473(12) (2015) 3951-3961.
Hathaway, et al., Thermally triggered release of the bacteriophage endolysin CHAPK and the bacteriocin lysostaphin for the control of methicillin resistant Staphylococcus aureus (MRSA). Journal of Controlled Release 245, 108-115 (2017).
Heim, et al., IL-12 promotes myeloid-derived suppressor cell recruitment and bacterial persistence during Staphylococcus aureus orthopedic implant infection, Journal of immunology 194(8) (2015) 3861-72.
Heim, et al., Interleukin-10 production by myeloid-derived suppressor cells contributes to bacterial persistence during Staphylococcus aureus orthopedic biofilm infection, Journal of leukocyte biology 98(6) (2015) 1003-13.
Heim, et al., Myeloid-derived suppressor cells contribute to Staphylococcus aureus orthopedic biofilm infection, Journal of immunology 192(8) (2014) 3778-92.
Inzana, et al., A novel murine model of established Staphylococcal bone infection in the presence of a fracture fixation plate to study therapies utilizing antibiotic-laden spacers after revision surgery. Bone 72, 128-136 (2015).
Inzana, et al., Biomaterials approaches to treating implant-associated osteomyelitis. Biomaterials 81, 58-71 (2016).
Kumar, Lysostaphin: an antistaphylococcal agent. Appl Microbiol Biotechnol 80, 555-561 (2008).
Raphel, M. Holodniy, S. B. Goodman, S. C. Heilshorn, Multifunctional coatings to simultaneously promote osseointegration and prevent infection of orthopaedic implants. Biomaterials 84, 301-314 (2016).
Moskowitz, M.R. Blaisse, R.E. Samuel, H.P. Hsu, M.B. Harris, S.D. Martin, J.C. Lee, M. Spector, P.T. Hammond, The effectiveness of the controlled release of gentamicin from poly electrolyte multilayers in the treatment of Staphylococcus aureus infection in a rabbit bone model, Biomaterials 31(23) (2010) 6019-30.
Hustedt, D.J. Blizzard, The Controversy Surrounding Bone Morphogenetic Proteins in the Spine: A Review of Current Research, The Yale Journal of Biology and Medicine 87(4) (2014) 549-561.
Johnson, et al., Hydrogel delivery of lysostaphin eliminates orthopedic implant infection by Staphylococcus aureus and supports fracture healing, Proceedings of the National Academy of Sciences of the United States of America 115(22) (2018) E4960-E4969.
Johnson, et al., Scaffold-based Anti-Infection Strategies in Bone Repair. Annals of biomedical engineering, (2014), 43, 515-528.
Blazanovic, H. Zhao, Y. Choi, W. Li, R. S. Salvat, D. C. Osipovitch, J. Fields, L. Moise, B. L. Berwin, S. N. Fiering, Structure-based redesign of lysostaphin yields potent antistaphylococcal enzymes that evade immune cell surveillance. Molecular therapy. Methods & clinical development 2, 15021 (2015).
Quickel, R. Selden, J. R. Caldwell, N. F. Nora, W. Schaffner, Efficacy and safety of topical lysostaphin treatment of persistent nasal carriage of Staphylococcus aureus. Applied microbiology 22, 446-450 (1971).
Park, K. E. Greenwood-Quaintance, A. N. Schuetz, J. N. Mandrekar, R. Patel, Activity of Tedizolid in Methicillin-Resistant Staphylococcus epidermidis Experimental Foreign Body-Associated Osteomyelitis. Antimicrobial agents and chemotherapy 61, (2017).
Kokai-Kun et al., Lysostaphin cream eradicates Staphylococcus aureus nasal colonization in a cotton rat model, Antimicrobial agents and chemotherapy 47(5) (2003) 1589-1597.
Kokai-Kun et al., Lysostaphin eradicates established Staphylococcus aureus biofilms in jugular vein catheterized mice. Journal of antimicrobial chemotherapy, dkp145 (2009), 94-100.
Kokai-Kun, et al., Lysostaphin as a treatment for systemic Staphylococcus aureus infection in a mouse model, Journal of antimicrobial chemotherapy 60(5) (2007) 1051-1059.
Lu, et al., Biomaterials with Antibacterial and Osteoinductive Properties to Repair Infected Bone Defects, International Journal of Molecular Sciences 17(3) (2016) 334.
Sok, M.C. Tria, C.E. Olingy, C.L. San Emeterio, E.A. Botchwey, Aspirin-Triggered Resolvin D1-modified materials promote the accumulation of pro-regenerative immune cell subsets and enhance vascular remodeling, Acta biomaterialia 53 (2017) 109-122.

(56) References Cited

OTHER PUBLICATIONS

Turner, B. Nedjai, T. Hurst, D.J. Pennington, Cytokines and chemokines: At the crossroads of cell signalling and inflammatory disease, Biochimica et biophysica acta 1843(11) (2014) 2563-2582.

Mohamed, M. I. Hamed, A. Panitch, M. N. Seleem, Targeting methicillin-resistant *Staphylococcus aureus* with short salt-resistant synthetic peptides. Antimicrobial agents and chemotherapy 58, 4113-4122 (2014).

Williams, M. A. Yakrus, M. J. Arduino, R. C. Cooksey, C. B. Crane, S. N. Banerjee, E. D. Hilborn, R. M. Donlan, Structural analysis of biofilm formation by rapidly and slowly growing nontuberculous mycobacteria. Appl Environ Microbiol 75, 2091-2098 (2009).

McHeyzer-Williams, S. Okitsu, N. Wang, L. McHeyzer-Williams, Molecular programming of B cell memory, Nat Rev Immunol 12(1) (2011) 24-34.

Climo, K. Ehlert, G. L. Archer, Mechanism and suppression of lysostaphin resistance in oxacillin-resistant *Staphylococcus aureus*. Antimicrobial agents and chemotherapy 45, 1431-1437 (2001).

Climo, R. L. Patron, B. P. Goldstein, G. L. Archer, Lysostaphin treatment of experimental methicillin-resistant *Staphylococcus aureus* aortic valve endocarditis. Antimicrobial agents and chemotherapy 42, 1355-1360 (1998).

Miao, et al., Lysostaphin-functionalized cellulose fibers with antistaphylococcal activity for wound healing applications. Biomaterials 32, 9557-9567 (2011).

Kiri, G. Archer, M. W. Climo, Combinations of Lysostaphin with P-Lactams Are Synergistic against Oxacillin-Resistant *Staphylococcus epidermidis*. Antimicrobial agents and chemotherapy 46, 2017-2020 (2002).

Nathan C., Neutrophils and immunity: challenges and opportunities, Nature Reviews Immunology 6 (2006) 173.

Neen, et al., Healos and bone marrow aspirate used for lumbar spine fusion: a case controlled study comparing healos with autograft, Spine 31(18) (2006) E636-40.

Oluola, L. Kong, M. Fein, L.E. Weisman, Lysostaphin in treatment of neonatal *Staphylococcus aureus* infection, Antimicrobial agents and chemotherapy 51(6) (2007) 2198-2200.

Szweda, G. Gorczyca, R. Tylingo, J. Kurlenda, J. Kwiecinski, S. Milewski, Chitosan—protein scaffolds loaded with lysostaphin as potential antistaphylococcal wound dressing materials. Journal of Applied Microbiology 117, 634-642 (2014).

Phelps, et al., Maleimide cross-linked bioactive PEG hydrogel exhibits improved reaction kinetics and cross-linking for cell encapsulation and in situ delivery. Advanced materials 24, 64-70, 62 (2012).

Phelps, et al., Vasculogenic bio-synthetic hydrogel for enhancement of pancreatic islet engraftment and function in type 1 diabetes. Biomaterials 34, 4602-4611 (2013).

Phelps, et al., Vasculogenic bio-synthetic hydrogel for enhancement of pancreatic islet engraftment and function in type 1 diabetes, Biomaterials 34(19) (2013) 4602-11.

Pribaz, et al., Mouse model of chronic post-arthroplasty infection: noninvasive in vivo bioluminescence imaging to monitor bacterial burden for long-term study. Journal of orthopaedic research: official publication of the Orthopaedic Research Society 30, 335-340 (2012).

Patron, M. W. Climo, B. P. Goldstein, G. L. Archer, Lysostaphin treatment of experimental aortic valve endocarditis caused by a *Staphylococcus aureus* isolate with reduced susceptibility to vancomycin. Antimicrobial agents and chemotherapy 43, 1754-1755 (1999).

Prabhakara, J.M. Harro, J.G. Leid, M. Harris, M.E. Shirtliff, Murine immune response to a chronic *Staphylococcus aureus* biofilm infection, Infection and immunity 79(4) (2011) 1789-96.

Roca, et al., The global threat of antimicrobial resistance: science for intervention. New Microbes New Infect 6, 22-29 (2015).

Goodman, Z. Yao, M. Keeney, F. Yang, The future of biologic coatings for orthopaedic implants. Biomaterials 34, 3174-3183 (2013).

Boyle-Vavra, R. B. Carey, R. S. Daum, Development of vancomycin and Tysostaphin resistance in a methicillin-resistant *Staphylococcus aureus* isolate. Journal of Antimicrobial Chemotherapy 48, 617-625 (2001).

Berrios-Torres, C. A. Umscheid, D. W. Bratzler, B. Leas, E. C. Stone, R. R. Kelz, C. E. Reinke, S. Morgan, J. S. Solomkin, J. E. Mazuski, E. P. Dellinger, K. M. F. Itani, E. F. Berbari, J. Segreti, J. Parvizi, J. Blanchard, G. Allen, J. Kluytmans, R. Donlan, W. P. Schecter, C. Healthcare Infection Control Practices Advisory, Centers for Disease Control and Prevention Guideline for the Prevention of Surgical Site Infection, 2017. JAMA Surg 152, 784-791 (2017).

Walsh, A. Shah, J. Mond, Improved pharmacokinetics and reduced antibody reactivity of lysostaphin conjugated to polyethylene glycol. Antimicrobial agents and chemotherapy 47, 554-558 (2003).

Guelcher, K.V. Brown, B. Li, T. Guda, B.H. Lee, J.C. Wenke, Dual-purpose bone grafts improve healing and reduce infection, Journal of orthopaedic trauma 25(8) (2011) 477-82.

Sabala, et al., Anti-staphylococcal activities of lysostaphin and LytM catalytic domain. BMC Microbiol 12, 97 (2012).

Sanchez, et al., Effects of local delivery of D-amino acids from biofilm-dispersive scaffolds on infection in contaminated rat segmental defects, Biomaterials 34(30) (2013) 7533-43.

Schindler, et al., Lysostaphin: a new bacteriolytic agent for the *Staphylococcus*. Proceedings of the National Academy of Sciences 51, 414-421 (1964).

Schwartz, et al., Prospective evaluation of chronic pain associated with posterior autologous iliac crest bone graft harvest and its effect on postoperative outcome, Health and quality of life outcomes 7 (2009) 49.

Shah, et al., Lysostaphin-coated catheters eradicate *Staphylocaccccus aureus* challenge and block surface colonization. Antimicrobial agents and chemotherapy 48, 2704-2707 (2004).

Shekaran, et al., Bone regeneration using an alpha 2 beta 1 integrin-specific hydrogel as a BMP-2 delivery vehicle, Biomaterials (2014), 35(21), 5453-5461.

Shekaran, et al., The effect of conditional inactivation of beta 1 integrins using twist 2 Cre, Osterix Cre and osteocalcin Cre lines on skeletal phenotype. Bone 68, 131-141 (2014).

Shi, et al., Monocyte recruitment during infection and inflammation, Nature Reviews Immunology 11 (2011) 762.

Slaughter, et al., Hydrogels in regenerative medicine. Advanced materials 21, 3307-3329 (2009).

Stallmann, et al., In vitro gentamicin release from commercially available calcium-phosphate bone substitutes influence of carrier type on duration of the release profile, BMC Musculoskelet Disord 7 (2006) 18.

Baba, O. Schneewind, Target cell specificity of a bacteriocin molecule: a C-terminal signal directs lysostaphin to the cell wall of *Staphylococcus aureus*. The EMBO journal 15, 4789 (1996).

Lee, J. R. Garcia, J. I. Paez, A. Singh, E. A. Phelps, S. Weis, Z. Shafiq, A. Shekaran, A. Del Campo, A. J. Garcia, Light-triggered in vivo activation of adhesive peptides regulates cell adhesion, inflammation and vascularization of biomaterials. Nature materials 14, 352-360 (2015).

Trampuz, et al., Diagnosis and treatment of infections associated with fracture-fixation devices. Injury 37 Suppl 2, S59-66 (2006).

Chadayammuri, M. Hake, C. Mauffrey, Innovative strategies for the management of long bone infection: a review of the Masquelet technique, Patient Safety in Surgery 9 (2015) 32.

Viswanathan, Off-label abuse of antibiotics by bacteria. Gut Microbes 5, 3-4 (2014).

Fischetti, Bacteriophage lysins as effective antibacterials, Current opinion in microbiology 11(5) (2008) 393-400.

Vidlak, et al., Infectious Dose Dictates the Host Response during *Staphylococcus Aureus* Orthopedic-Implant Biofilm Infection, Infection and immunity 84(7) (2016) 1957-65.

Forster, O. Mayer, J. J. Curtin, S. M. Lehman, R. M. Donlan, et al. Bacteriophage cocktail for the prevention of biofilm formation by Pseudomonas aeruginosa on catheters in an in vitro model system. Antimicrobial agents and chemotherapy 54, 397-404 (2010).

(56) References Cited

OTHER PUBLICATIONS

Schaffner, M. Melly, M. Koenig, Lysostaphin: an enzymatic approach to staphylococcal disease. II. In vivo studies, The Yale journal of biology and medicine 39(4) (1967) 230.

Wagner, et al., Diminished bone regeneration after debridement of posttraumatic osteomyelitis is accompanied by altered cytokine levels, elevated B cell activity, and increased osteoclast activity, Journal of orthopaedic research: official publication of the Orthopaedic Research Society 35(11) (2017) 2425-2434.

Weaver, et al., Vasculogenic hydrogel enhances islet survival, engraftment, and function in leading extrahepatic sites. Science advances 3, e1700184 (2017).

Willis-Owen, et al., Factors affecting the incidence of infection in hip and knee replacement, Journal of Bone &amp; Joint Surgery, British vol. 92-B(8) (2010) 1128.

Windolf, et al., Lysostaphin-coated titan-implants preventing localized osteitis by *Staphylococcus aureus* in a mouse model. PloS one 9, e115940 (2014).

Wu, et al., Lysostaphin Disrupts *Staphylococcus aureus* and *Staphylococcus epidermidis* Biofilms on Artificial Surfaces. Antimicrobial agents and chemotherapy 47, 3407-3414 (2003).

Xue, et al., A novel controlled-release system for antibacterial enzyme lysostaphin delivery using hydroxyapatite/chitosan composite bone cement. PloS one 9, e113797 (2014).

Zheng, W. Yin, J.N. Zara, W. Li, J. Kwak, R. Mamidi, M. Lee, R.K. Siu, R. Ngo, J. Wang, D. Carpenter, X. Zhang, B. Wu, K. Ting, C. Soo, The use of BMP-2 coupled—Nanosilver-PLGA composite grafts to induce bone repair in grossly infected segmental defects, Biomaterials 31(35) (2010) 9293-300.

Zhao, et al., Depletion of T cell epitopes in lysostaphin mitigates anti-drug antibody response and enhances antibacterial efficacy in vivo. Chem Biol 22, 629-639 (2015).

\* cited by examiner

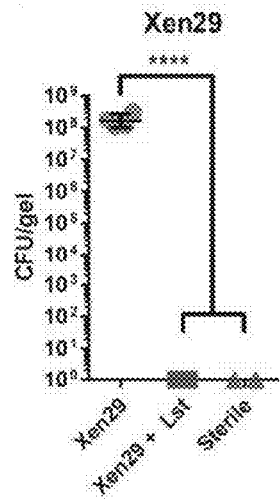 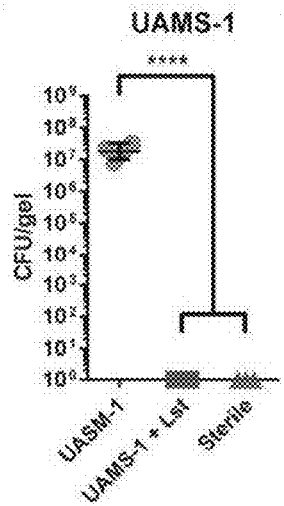 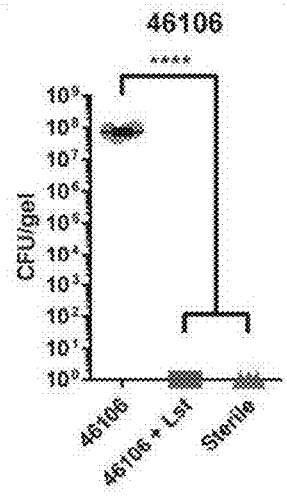 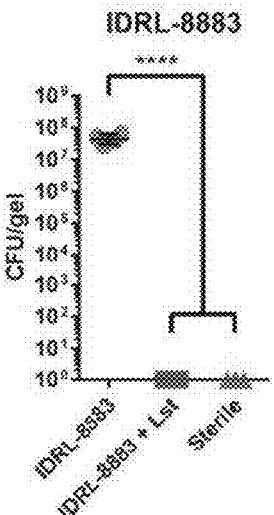
FIGURE 2A     FIGURE 2B     FIGURE 2C     FIGURE 2D
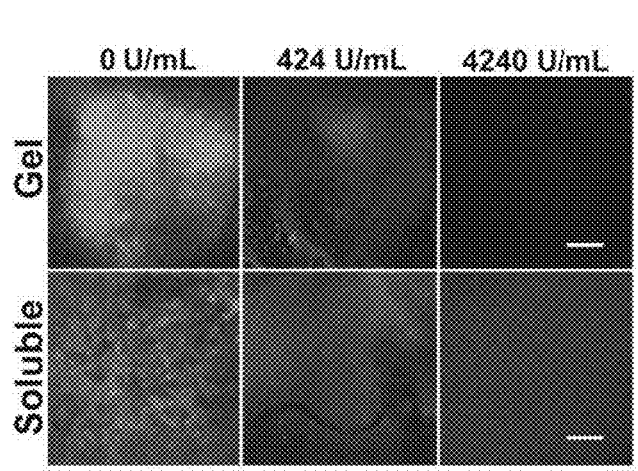 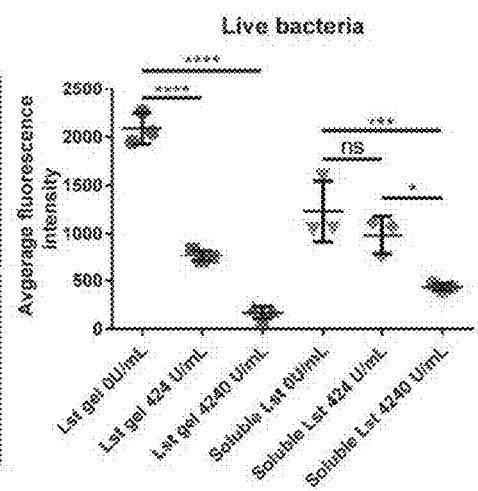
FIGURE 2E     FIGURE 2F

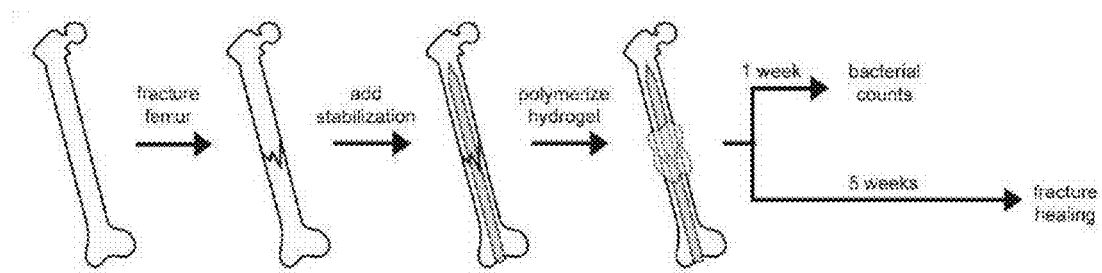
FIGURE 3A
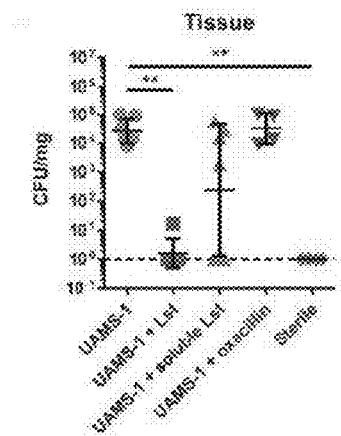
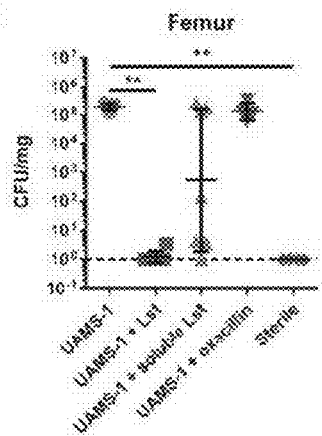
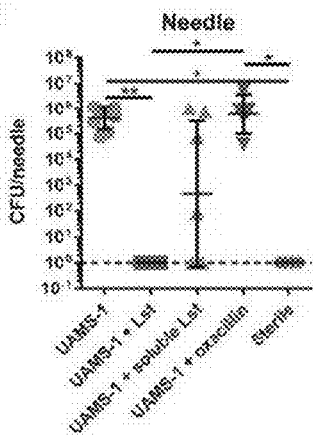
FIGURE 3B        FIGURE 3C        FIGURE 3D
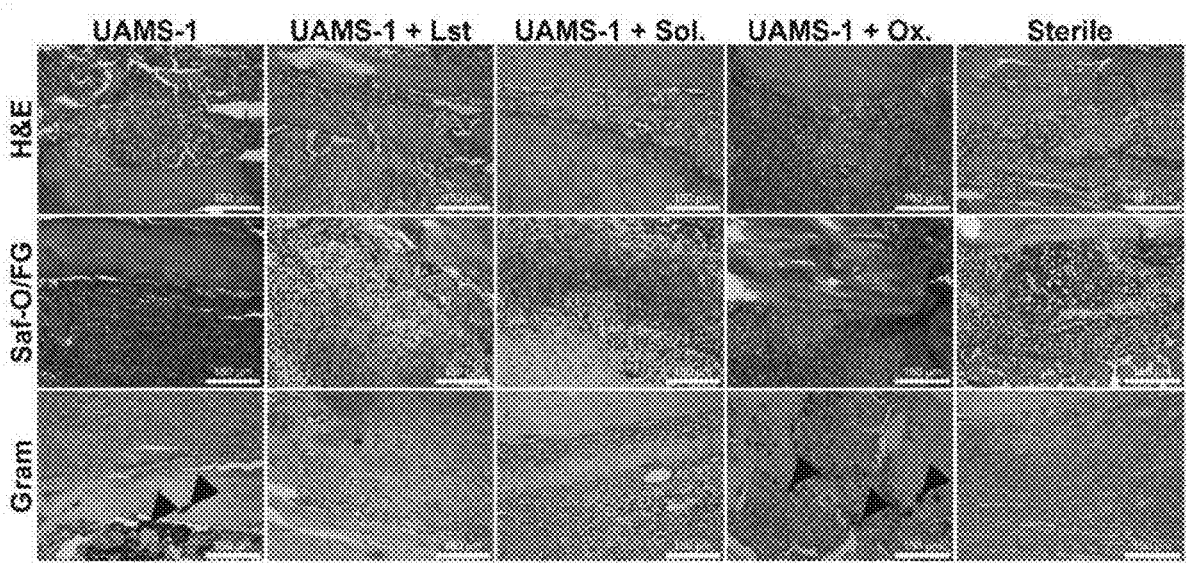
FIGURE 3E

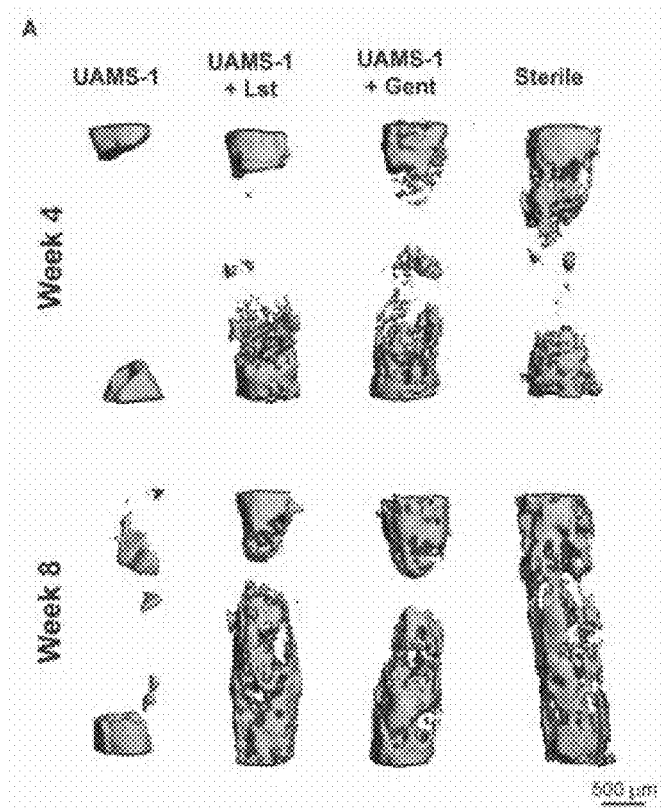
FIGURE 9A
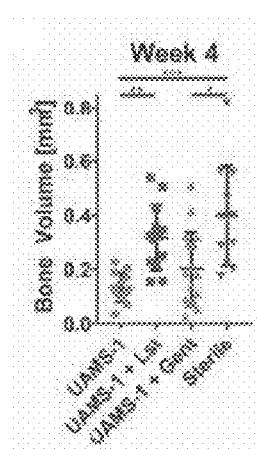 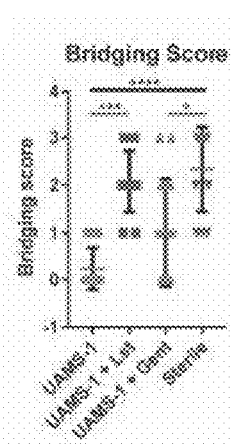 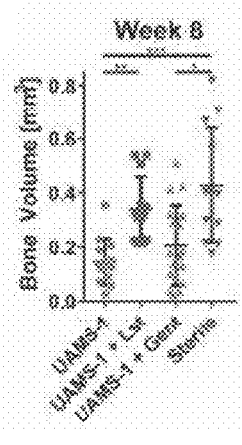 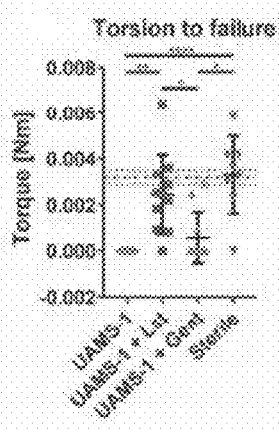
FIGURE 9B　　　FIGURE 9C　　　FIGURE 9D　　　FIGURE 9E

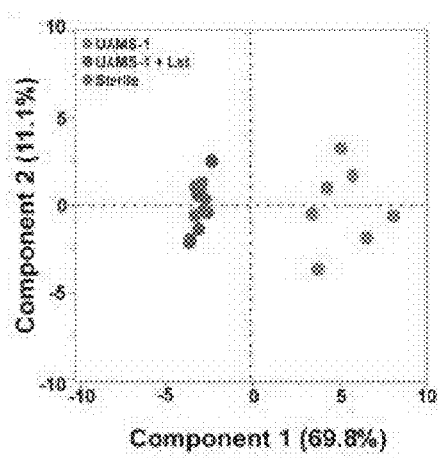
FIGURE 10B
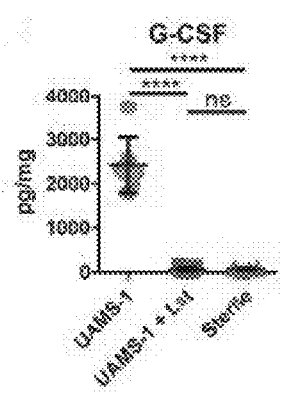 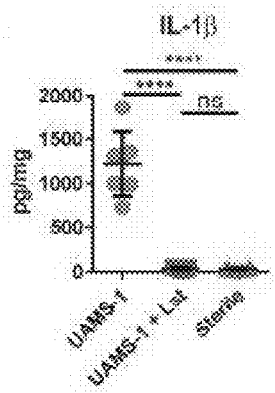 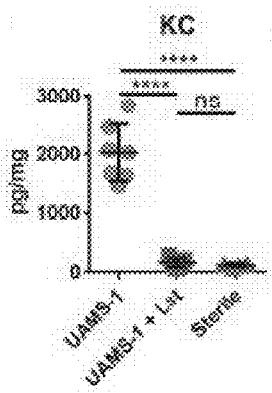 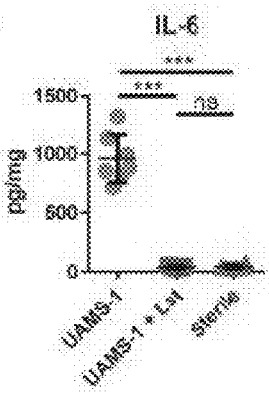
FIGURE 10C  FIGURE 10D  FIGURE 10E  FIGURE 10F
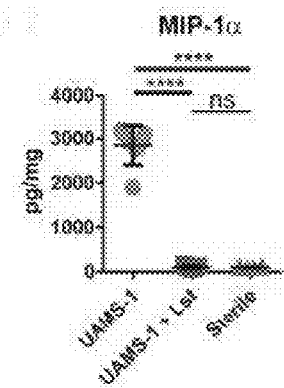 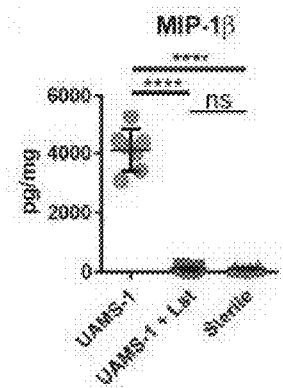 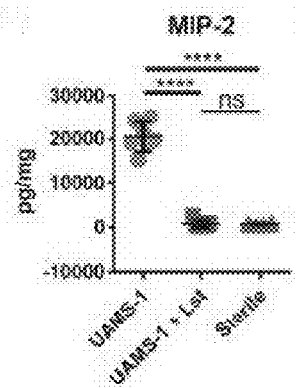 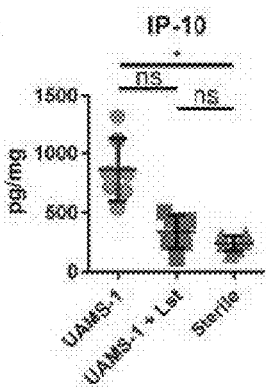
FIGURE 10G  FIGURE 10H  FIGURE 10I  FIGURE 10J

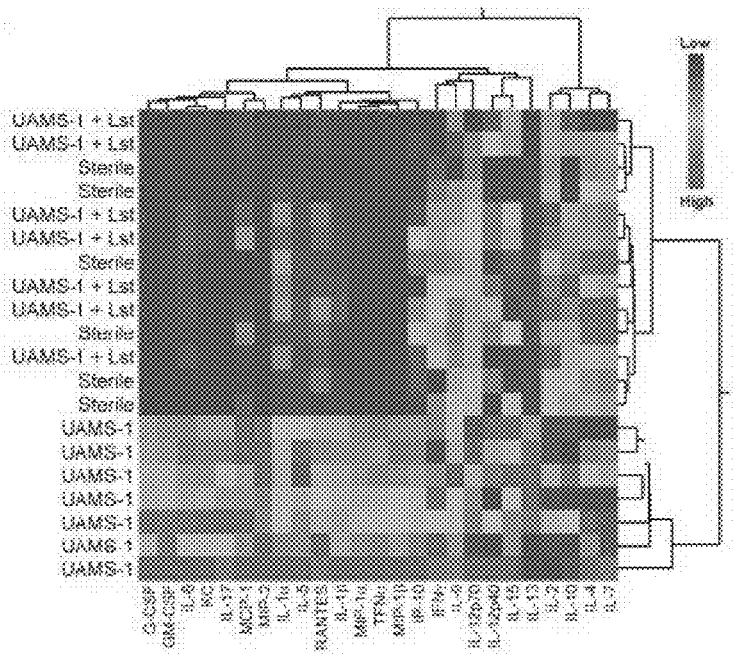
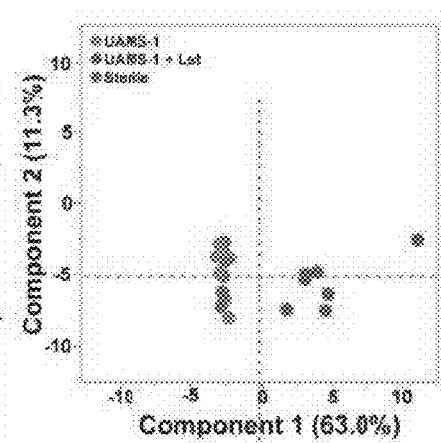
FIGURE 11B
FIGURE 11A
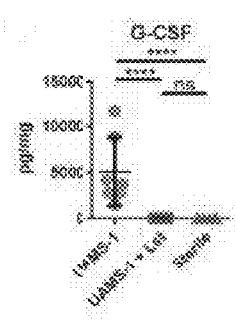 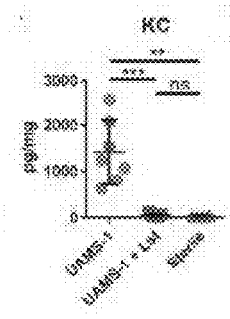 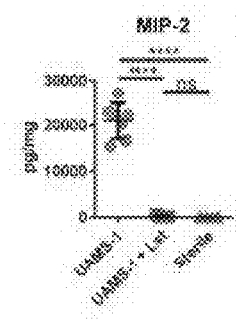 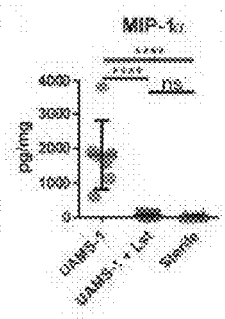 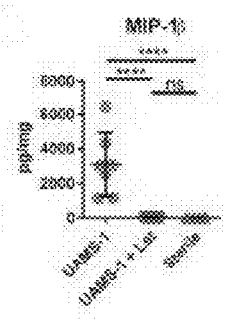
FIGURE 11C    FIGURE 11D    FIGURE 11E    FIGURE 11F    FIGURE 11G

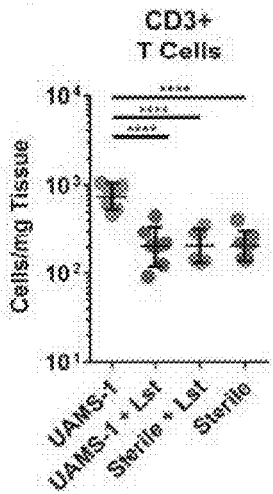
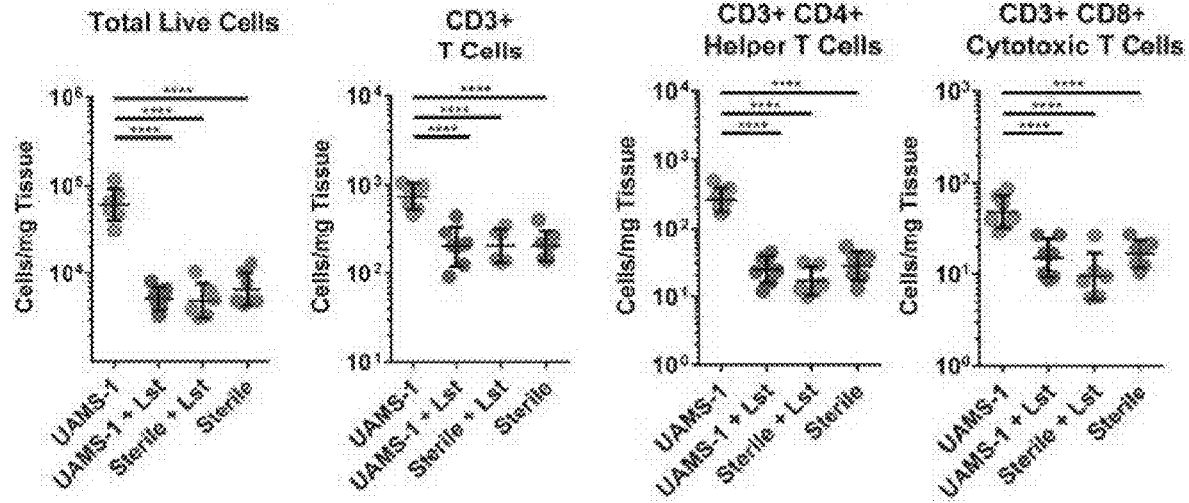
FIGURE 12A  FIGURE 12B  FIGURE 12C  FIGURE 12D
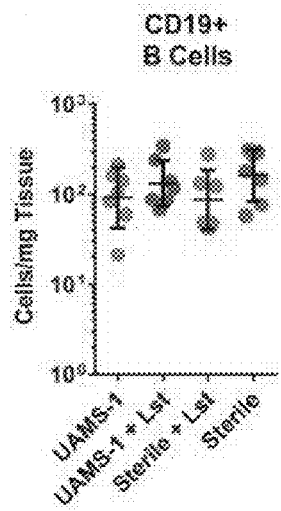
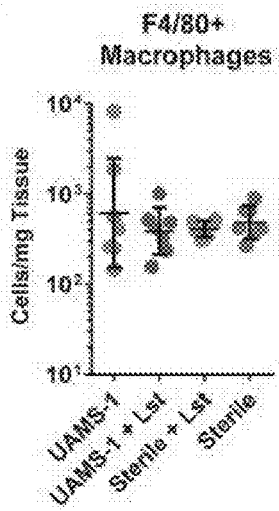
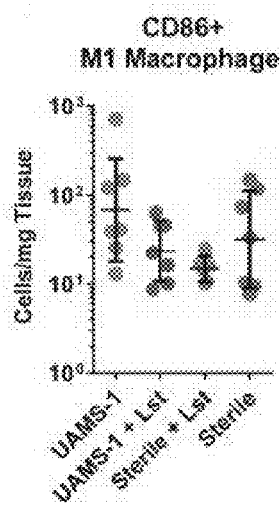
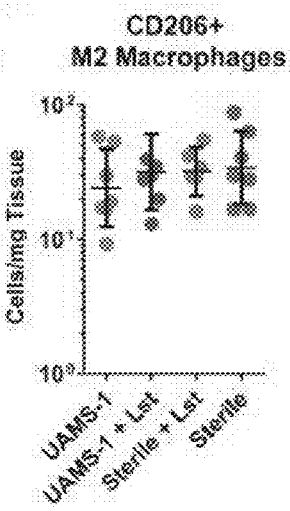
FIGURE 12E  FIGURE 12F  FIGURE 12G  FIGURE 12H

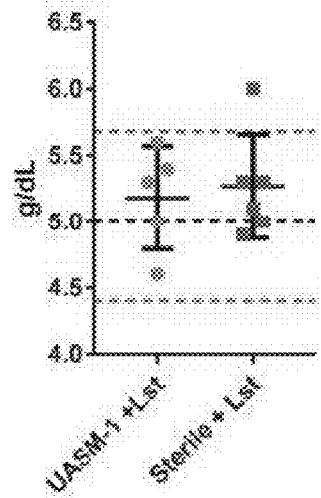 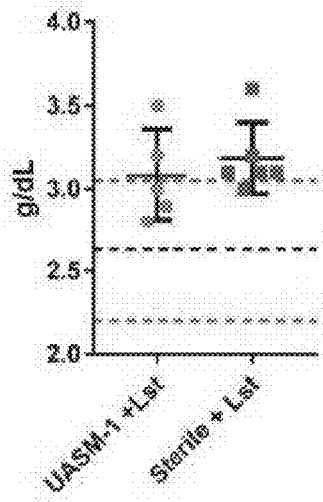 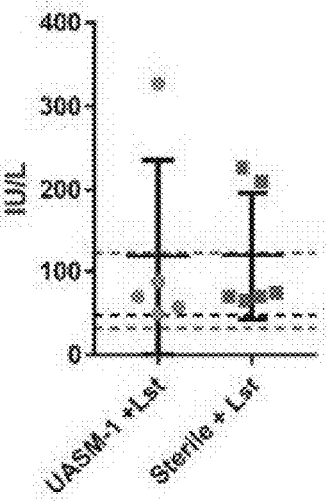
FIGURE 15A  FIGURE 15B  FIGURE 15C
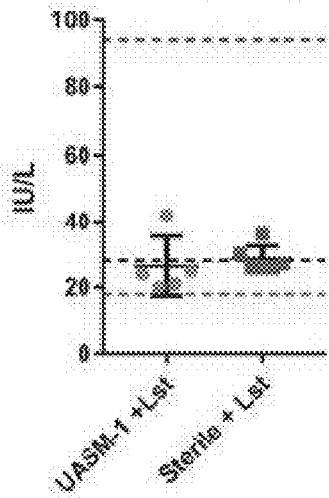 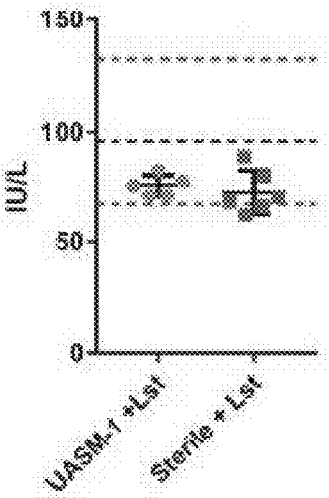
FIGURE 15D  FIGURE 15E

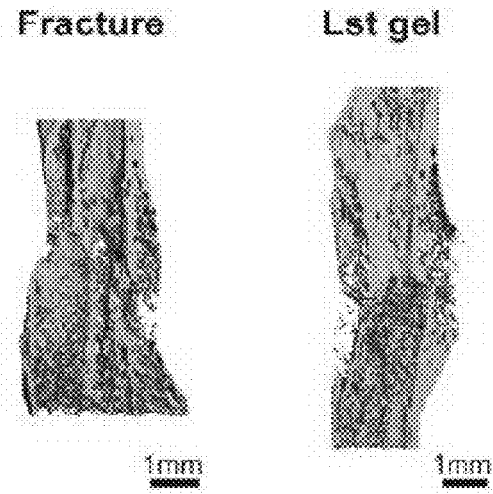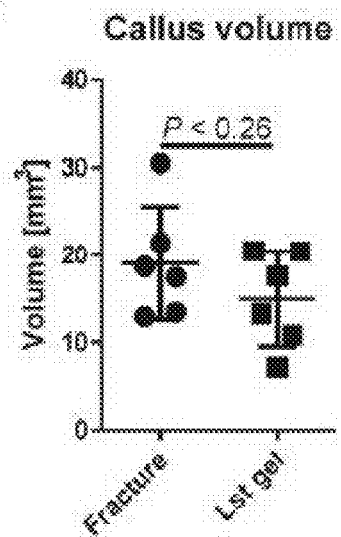
FIGURE 23A
FIGURE 23B
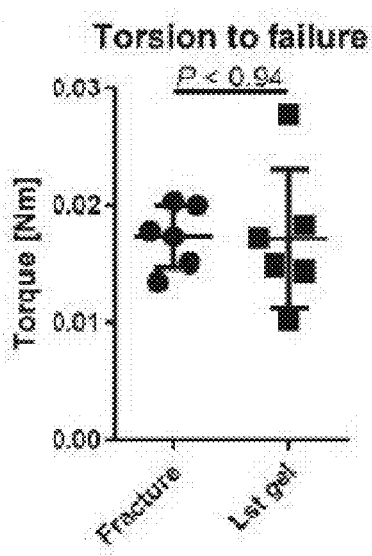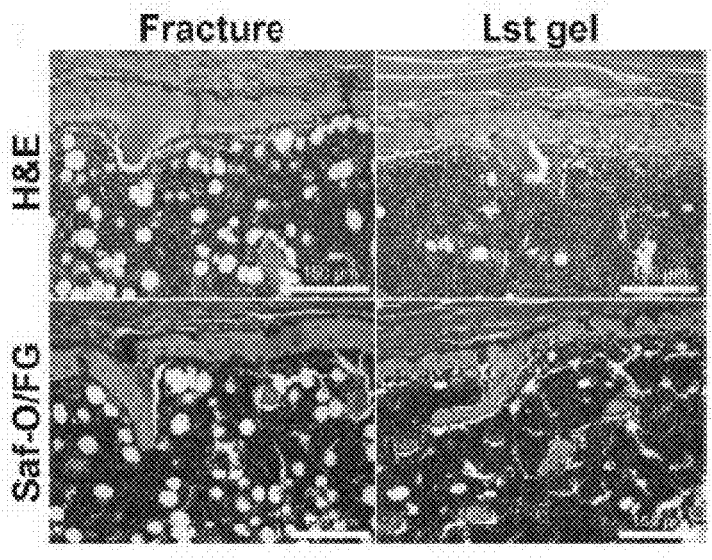
FIGURE 23C
FIGURE 23D

SEQUENCE LISTING

```
<160> NUMBER OF SEQ ID NOS: 59

<210> SEQ ID NO 1
<211> LENGTH: 7
<212> TYPE: PRT
<213> ORGANISM: Artificial Sequence
<220> FEATURE:
<223> OTHER INFORMATION: Synthetic construct

<400> SEQUENCE: 1

Gly Arg Gly Asp Ser Pro Cys
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic construct

<400> SEQUENCE: 2

Cys Arg Gly Asp Ser
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic construct

<400> SEQUENCE: 3

Cys Arg Gly Asp Ser Pro
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic construct

<400> SEQUENCE: 4

Cys Pro His Ser Arg Asn
1               5

<210> SEQ ID NO 5
<211> LENGTH: 10
<212> TYPE: PRT
<213> ORGANISM: Artificial Sequence
<220> FEATURE:
<223> OTHER INFORMATION: Synthetic construct
```

```
<400> SEQUENCE: 5

Cys Gly Trp Gly Gly Arg Gly Asp Ser Pro
1               5                   10

<210> SEQ ID NO 6
<211> LENGTH: 16
<212> TYPE: PRT
<213> ORGANISM: Artificial Sequence
<220> FEATURE:
<223> OTHER INFORMATION: Synthetic construct

<400> SEQUENCE: 6

Cys Gly Gly Ser Ile Asp Gln Val Glu Pro Tyr Ser Ser Thr Ala Gln
1               5                   10                  15

<210> SEQ ID NO 7
<211> LENGTH: 13
<212> TYPE: PRT
<213> ORGANISM: Artificial Sequence
<220> FEATURE:
<223> OTHER INFORMATION: Synthetic construct

<400> SEQUENCE: 7

Cys Gly Gly Arg Asn Ile Ala Glu Ile Ile Lys Asp Ile
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Synthetic construct

<400> SEQUENCE: 8

Cys Gly Gly Asp Ile Thr Tyr Val Arg Leu Lys Phe
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Synthetic construct

<400> SEQUENCE: 9

Cys Gly Gly Asp Ile Thr Val Thr Leu Asn Arg Leu
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Synthetic construct

<400> SEQUENCE: 10

Cys Gly Gly Arg Tyr Val Val Leu Pro Arg
1               5                   10

<210> SEQ ID NO 11
<211> LENGTH: 15
<212> TYPE: PRT
<213> ORGANISM: Artificial Sequence
<220> FEATURE:
<223> OTHER INFORMATION: Synthetic construct

<400> SEQUENCE: 11
```

Cys Gly Gly Lys Ala Phe Asp Ile Thr Tyr Val Arg Leu Lys Phe
1               5                   10                  15

<210> SEQ ID NO 12
<211> LENGTH: 14
<212> TYPE: PRT
<213> ORGANISM: Artificial Sequence
<220> FEATURE:
<223> OTHER INFORMATION: Synthetic construct

<400> SEQUENCE: 12

Cys Gly Gly Glu Gly Tyr Gly Glu Gly Tyr Ile Gly Ser Arg
1               5                   10

<210> SEQ ID NO 13
<211> LENGTH: 23
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (16)..(16)
<223> OTHER INFORMATION: Xaa can be any naturally occurring amino acid

<400> SEQUENCE: 13

Cys Gly Gly Ala Thr Leu Gln Leu Gln Glu Gly Arg Leu His Phe Xaa
1               5                   10                  15

Phe Asp Leu Gly Lys Gly Arg
            20

<210> SEQ ID NO 14
<211> LENGTH: 15
<212> TYPE: PRT
<213> ORGANISM: Artificial Sequence
<220> FEATURE:
<223> OTHER INFORMATION: Synthetic construct

<400> SEQUENCE: 14

Cys Gly Gly Ser Tyr Trp Tyr Arg Ile Glu Ala Ser Arg Thr Gly
1               5                   10                  15

<210> SEQ ID NO 15
<211> LENGTH: 17
<212> TYPE: PRT
<213> ORGANISM: Artificial Sequence
<220> FEATURE:
<223> OTHER INFORMATION: Synthetic construct

<400> SEQUENCE: 15

Cys Gly Gly Gly Glu Phe Tyr Phe Asp Leu Arg Leu Lys Gly Asp Lys
1               5                   10                  15

Tyr

<210> SEQ ID NO 16
<211> LENGTH: 16
<212> TYPE: PRT
<213> ORGANISM: Artificial Sequence
<220> FEATURE:
<223> OTHER INFORMATION: Synthetic construct

<400> SEQUENCE: 16

Cys Lys Gly Gly Asn Gly Glu Pro Arg Gly Asp Thr Tyr Arg Ala Tyr
1               5                   10                  15

```
<210> SEQ ID NO 17
<211> LENGTH: 16
<212> TYPE: PRT
<213> ORGANISM: Artificial Sequence
<220> FEATURE:
<223> OTHER INFORMATION: Synthetic construct

<400> SEQUENCE: 17

Cys Lys Gly Gly Pro Gln Val Thr Arg Gly Asp Val Phe Thr Met Pro
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Synthetic construct

<400> SEQUENCE: 18

Cys Gly Gly Asn Arg Trp His Ser Ile Tyr Ile Thr Arg Phe Gly
1               5                   10                  15

<210> SEQ ID NO 19
<211> LENGTH: 14
<212> TYPE: PRT
<213> ORGANISM: Artificial Sequence
<220> FEATURE:
<223> OTHER INFORMATION: Synthetic construct

<400> SEQUENCE: 19

Cys Gly Gly Ala Ser Ile Lys Val Ala Val Ser Ala Asp Arg
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Synthetic construct

<400> SEQUENCE: 20

Cys Gly Gly Thr Thr Val Lys Tyr Ile Phe Arg
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Synthetic construct

<400> SEQUENCE: 21

Cys Gly Gly Ser Ile Lys Ile Arg Gly Thr Tyr Ser
1               5                   10

<210> SEQ ID NO 22
<211> LENGTH: 9
<212> TYPE: PRT
<213> ORGANISM: Artificial Sequence
<220> FEATURE:
<223> OTHER INFORMATION: Synthetic construct

<400> SEQUENCE: 22

Cys Gly Gly Ser Ile Asn Asn Asn Arg
1               5

<210> SEQ ID NO 23
```

```
<211> LENGTH: 12
<212> TYPE: PRT
<213> ORGANISM: Artificial Sequence
<220> FEATURE:
<223> OTHER INFORMATION: Synthetic construct

<400> SEQUENCE: 23

Cys Gly Gly Ser Asp Pro Gly Tyr Ile Gly Ser Arg
1               5                   10

<210> SEQ ID NO 24
<211> LENGTH: 6
<212> TYPE: PRT
<213> ORGANISM: Artificial Sequence
<220> FEATURE:
<223> OTHER INFORMATION: Synthetic construct

<400> SEQUENCE: 24

Cys Tyr Ile Gly Ser Arg
1               5

<210> SEQ ID NO 25
<211> LENGTH: 16
<212> TYPE: PRT
<213> ORGANISM: Artificial Sequence
<220> FEATURE:
<223> OTHER INFORMATION: Synthetic construct

<400> SEQUENCE: 25

Cys Gly Gly Thr Pro Gly Pro Gln Gly Ile Ala Gly Gln Gly Val Val
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: Synthetic construct

<400> SEQUENCE: 26

Cys Gly Gly Thr Pro Gly Pro Gln Gly Ile Ala Gly Gln Arg Val Val
1               5                   10                  15

<210> SEQ ID NO 27
<211> LENGTH: 10
<212> TYPE: PRT
<213> ORGANISM: Artificial Sequence
<220> FEATURE:
<223> OTHER INFORMATION: Synthetic construct

<400> SEQUENCE: 27

Cys Gly Gly Met Asn Tyr Tyr Ser Asn Ser
1               5                   10

<210> SEQ ID NO 28
<211> LENGTH: 15
<212> TYPE: PRT
<213> ORGANISM: Artificial Sequence
<220> FEATURE:
<223> OTHER INFORMATION: Synthetic construct

<400> SEQUENCE: 28

Cys Gly Gly Lys Lys Gln Arg Phe Arg His Arg Asn Arg Lys Gly
1               5                   10                  15

<210> SEQ ID NO 29
<211> LENGTH: 22
```

```
<212> TYPE: PRT
<213> ORGANISM: Artificial Sequence
<220> FEATURE:
<223> OTHER INFORMATION: Synthetic construct

<400> SEQUENCE: 29

Cys Arg Gly Asp Gly Gly Gly Gly Gly Gly Gly Gly Gly Gly
1               5                   10                  15

Gly Pro His Ser Arg Asn
            20

<210> SEQ ID NO 30
<211> LENGTH: 19
<212> TYPE: PRT
<213> ORGANISM: Artificial Sequence
<220> FEATURE:
<223> OTHER INFORMATION: Synthetic construct

<400> SEQUENCE: 30

Cys Pro His Ser Arg Asn Ser Gly Ser Gly Ser Gly Ser Gly
1               5                   10                  15

Arg Gly Asp

<210> SEQ ID NO 31
<211> LENGTH: 20
<212> TYPE: PRT
<213> ORGANISM: Artificial Sequence
<220> FEATURE:
<223> OTHER INFORMATION: Synthetic construct

<400> SEQUENCE: 31

Ala Cys Glu Thr Tyr Leu Ala Thr Glu Asp Gly Cys Tyr Gly Arg Gly
1               5                   10                  15

Asp Ser Pro Gly
            20

<210> SEQ ID NO 32
<211> LENGTH: 18
<212> TYPE: PRT
<213> ORGANISM: Artificial Sequence
<220> FEATURE:
<223> OTHER INFORMATION: Synthetic construct

<400> SEQUENCE: 32

Gly Pro Pro Gly Pro Pro Gly Pro Pro Gly Pro Pro Gly Pro Pro Gly
1               5                   10                  15

Pro Cys

<210> SEQ ID NO 33
<211> LENGTH: 5
<212> TYPE: PRT
<213> ORGANISM: Artificial Sequence
<220> FEATURE:
<223> OTHER INFORMATION: Synthetic construct

<400> SEQUENCE: 33

Cys Arg Asp Gly Ser
1               5

<210> SEQ ID NO 34
<211> LENGTH: 12
<212> TYPE: PRT
<213> ORGANISM: Artificial Sequence
<220> FEATURE:
<223> OTHER INFORMATION: Synthetic construct
```

```
<400> SEQUENCE: 34

Cys Tyr Cys Leu Ile Cys Arg Gly Asp Phe Asp Cys
1               5                   10

<210> SEQ ID NO 35
<211> LENGTH: 15
<212> TYPE: PRT
<213> ORGANISM: Artificial Sequence
<220> FEATURE:
<223> OTHER INFORMATION: Synthetic construct

<400> SEQUENCE: 35

Cys Gly Gly Arg Lys Arg Leu Gln Val Gln Leu Ser Ile Arg Thr
1               5                   10                  15

<210> SEQ ID NO 36
<211> LENGTH: 6
<212> TYPE: PRT
<213> ORGANISM: Artificial Sequence
<220> FEATURE:
<223> OTHER INFORMATION: Synthetic construct

<400> SEQUENCE: 36

Cys Ile Lys Val Ala Val
1               5

<210> SEQ ID NO 37
<211> LENGTH: 15
<212> TYPE: PRT
<213> ORGANISM: Artificial Sequence
<220> FEATURE:
<223> OTHER INFORMATION: Synthetic construct

<400> SEQUENCE: 37

Cys Gly Gly Ala Ala Ser Ile Lys Val Ala Val Ser Ala Asp Arg
1               5                   10                  15

<210> SEQ ID NO 38
<211> LENGTH: 11
<212> TYPE: PRT
<213> ORGANISM: Artificial Sequence
<220> FEATURE:
<223> OTHER INFORMATION: Synthetic construct

<400> SEQUENCE: 38

Cys Gly Gly Lys Arg Thr Gly Gln Tyr Lys Leu
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Synthetic construct

<400> SEQUENCE: 39

Cys Gly Gly Thr Tyr Arg Ser Arg Lys Tyr
1               5                   10

<210> SEQ ID NO 40
<211> LENGTH: 46
<212> TYPE: PRT
<213> ORGANISM: Artificial Sequence
<220> FEATURE:
<223> OTHER INFORMATION: Synthetic construct
<220> FEATURE:
```

```
<221> NAME/KEY: MISC_FEATURE
<222> LOCATION: (26)..(26)
<223> OTHER INFORMATION: Xaa is hydroxyproline

<400> SEQUENCE: 40

Cys Gly Gly Tyr Gly Gly Pro Gly Pro Pro Gly Pro Pro Gly Pro
1               5                   10                  15

Pro Gly Pro Pro Gly Pro Pro Gly Phe Xaa Gly Glu Arg Pro Pro Gly
            20                  25                  30

Pro Pro Gly Pro Pro Gly Pro Pro Gly Pro Pro Gly Pro Cys
        35                  40                  45

<210> SEQ ID NO 41
<211> LENGTH: 20
<212> TYPE: PRT
<213> ORGANISM: Artificial Sequence
<220> FEATURE:
<223> OTHER INFORMATION: Synthetic construct

<400> SEQUENCE: 41

Cys Gly Gly Lys Arg Thr Gly Gln Tyr Lys Leu Gly Ser Lys Thr Gly
1               5                   10                  15

Pro Gly Gln Lys
            20

<210> SEQ ID NO 42
<211> LENGTH: 14
<212> TYPE: PRT
<213> ORGANISM: Artificial Sequence
<220> FEATURE:
<223> OTHER INFORMATION: Synthetic construct

<400> SEQUENCE: 42

Gln Ala Lys His Lys Gln Arg Lys Arg Leu Lys Ser Ser Cys
1               5                   10

<210> SEQ ID NO 43
<211> LENGTH: 17
<212> TYPE: PRT
<213> ORGANISM: Artificial Sequence
<220> FEATURE:
<223> OTHER INFORMATION: Synthetic construct

<400> SEQUENCE: 43

Ser Pro Lys His His Ser Gln Arg Ala Arg Lys Lys Lys Asn Lys Asn
1               5                   10                  15

Cys

<210> SEQ ID NO 44
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (4)..(4)
<223> OTHER INFORMATION: Xaa can be Iso, Val, Leu, Phe, Cys, Gly, Met,
      or Ala
<220> FEATURE:
<221> NAME/KEY: misc_feature
<222> LOCATION: (5)..(6)
<223> OTHER INFORMATION: Xaa can be Lys, Arg, or His
<220> FEATURE:
<221> NAME/KEY: misc_feature
<222> LOCATION: (7)..(7)
<223> OTHER INFORMATION: Xaa can be Iso, Val, Leu, Phe, Cys, Gly, Met,
``` or Ala
<220> FEATURE:
<221> NAME/KEY: misc_feature
<222> LOCATION: (8)..(8)
<223> OTHER INFORMATION: Xaa can be Lys, Arg, or His
<220> FEATURE:
<221> NAME/KEY: misc_feature
<222> LOCATION: (9)..(9)
<223> OTHER INFORMATION: Xaa can be Iso, Val, Leu, Phe, Cys, Gly, Met,
       or Ala

<400> SEQUENCE: 44

Cys Gly Gly Xaa Xaa Xaa Xaa Xaa Xaa
1               5

<210> SEQ ID NO 45
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (4)..(4)
<223> OTHER INFORMATION: Xaa can be Iso, Val, Leu, Phe, Cys, Gly, Met,
       or Ala
<220> FEATURE:
<221> NAME/KEY: misc_feature
<222> LOCATION: (5)..(7)
<223> OTHER INFORMATION: Xaa can be Lys, Arg, or His
<220> FEATURE:
<221> NAME/KEY: misc_feature
<222> LOCATION: (8)..(9)
<223> OTHER INFORMATION: Xaa can be Iso, Val, Leu, Phe, Cys, Gly, Met,
       or Ala
<220> FEATURE:
<221> NAME/KEY: misc_feature
<222> LOCATION: (10)..(10)
<223> OTHER INFORMATION: Xaa can be Lys, Arg, or His
<220> FEATURE:
<221> NAME/KEY: misc_feature
<222> LOCATION: (11)..(11)
<223> OTHER INFORMATION: Xaa can be Iso, Val, Leu, Phe, Cys, Gly, Met,
       or Ala

<400> SEQUENCE: 45

Cys Gly Gly Xaa Xaa Xaa Xaa Xaa Xaa Xaa Xaa
1               5                   10

<210> SEQ ID NO 46
<211> LENGTH: 16
<212> TYPE: PRT
<213> ORGANISM: Artificial Sequence
<220> FEATURE:
<223> OTHER INFORMATION: Synthetic construct

<400> SEQUENCE: 46

Gly Cys Arg Asp Gly Pro Gln Gly Ile Trp Gly Gln Asp Arg Cys Gly
1               5                   10                  15

<210> SEQ ID NO 47
<211> LENGTH: 16
<212> TYPE: PRT
<213> ORGANISM: Artificial Sequence
<220> FEATURE:
<223> OTHER INFORMATION: Synthetic construct

<400> SEQUENCE: 47

Gly Cys Arg Asp Gly Pro Gln Gly Ile Ala Gly Gln Asp Arg Cys Gly
1               5                   10                  15

<210> SEQ ID NO 48
<211> LENGTH: 16
<212> TYPE: PRT
<213> ORGANISM: Artificial Sequence
<220> FEATURE:
<223> OTHER INFORMATION: Synthetic construct

<400> SEQUENCE: 48

Gly Cys Arg Asp Val Pro Met Ser Met Arg Gly Gly Asp Arg Cys Gly
1               5                   10                  15

<210> SEQ ID NO 49
<211> LENGTH: 16
<212> TYPE: PRT
<213> ORGANISM: Artificial Sequence
<220> FEATURE:
<223> OTHER INFORMATION: Synthetic construct

<400> SEQUENCE: 49

Gly Cys Arg Asp Ile Pro Val Ser Leu Arg Ser Gly Asp Arg Cys Gly
1               5                   10                  15

<210> SEQ ID NO 50
<211> LENGTH: 16
<212> TYPE: PRT
<213> ORGANISM: Artificial Sequence
<220> FEATURE:
<223> OTHER INFORMATION: Synthetic construct

<400> SEQUENCE: 50

Gly Cys Arg Asp Arg Pro Phe Ser Met Ile Met Gly Asp Arg Cys Gly
1               5                   10                  15

<210> SEQ ID NO 51
<211> LENGTH: 16
<212> TYPE: PRT
<213> ORGANISM: Artificial Sequence
<220> FEATURE:
<223> OTHER INFORMATION: Synthetic construct

<400> SEQUENCE: 51

Gly Cys Arg Asp Val Pro Leu Ser Leu Thr Met Gly Asp Arg Cys Gly
1               5                   10                  15

<210> SEQ ID NO 52
<211> LENGTH: 16
<212> TYPE: PRT
<213> ORGANISM: Artificial Sequence
<220> FEATURE:
<223> OTHER INFORMATION: Synthetic construct

<400> SEQUENCE: 52

Gly Cys Arg Asp Val Pro Leu Ser Leu Tyr Ser Gly Asp Arg Cys Gly
1               5                   10                  15

<210> SEQ ID NO 53
<211> LENGTH: 16
<212> TYPE: PRT
<213> ORGANISM: Artificial Sequence
<220> FEATURE:
<223> OTHER INFORMATION: Synthetic construct

<400> SEQUENCE: 53

Gly Cys Arg Asp Ile Pro Glu Ser Leu Arg Ala Gly Asp Arg Cys Gly
1               5                   10                  15

<210> SEQ ID NO 54

```
<211> LENGTH: 18
<212> TYPE: PRT
<213> ORGANISM: Artificial Sequence
<220> FEATURE:
<223> OTHER INFORMATION: Synthetic construct

<400> SEQUENCE: 54

Gly Cys Arg Asp Ser Gly Glu Ser Pro Ala Tyr Tyr Thr Ala Asp Arg
1               5                   10                  15

Cys Gly

<210> SEQ ID NO 55
<211> LENGTH: 18
<212> TYPE: PRT
<213> ORGANISM: Artificial Sequence
<220> FEATURE:
<223> OTHER INFORMATION: Synthetic construct

<400> SEQUENCE: 55

Gly Cys Arg Asp Gly Gly Tyr Ala Glu Leu Arg Met Gly Gly Asp Arg
1               5                   10                  15

Cys Gly

<210> SEQ ID NO 56
<211> LENGTH: 18
<212> TYPE: PRT
<213> ORGANISM: Artificial Sequence
<220> FEATURE:
<223> OTHER INFORMATION: Synthetic construct

<400> SEQUENCE: 56

Gly Cys Arg Asp Gly Gly Pro Leu Gly Leu Tyr Ala Gly Gly Asp Arg
1               5                   10                  15

Cys Gly

<210> SEQ ID NO 57
<211> LENGTH: 16
<212> TYPE: PRT
<213> ORGANISM: Artificial Sequence
<220> FEATURE:
<223> OTHER INFORMATION: Synthetic construct

<400> SEQUENCE: 57

Gly Cys Arg Asp Gly Pro Leu Gly Leu Trp Ala Arg Asp Arg Cys Gly
1               5                   10                  15

<210> SEQ ID NO 58
<211> LENGTH: 246
<212> TYPE: PRT
<213> ORGANISM: Bacillus sphaericus

<400> SEQUENCE: 58

Ala Ala Thr His Glu His Ser Ala Gln Trp Leu Asn Asn Tyr Lys Lys
1               5                   10                  15

Gly Tyr Gly Tyr Gly Pro Tyr Pro Leu Gly Ile Asn Gly Gly Met His
            20                  25                  30

Tyr Gly Val Asp Phe Phe Met Asn Ile Gly Thr Pro Val Lys Ala Ile
        35                  40                  45

Ser Ser Gly Lys Ile Val Glu Ala Gly Trp Ser Asn Tyr Gly Gly Gly
    50                  55                  60

Asn Gln Ile Gly Leu Ile Glu Asn Asp Gly Val His Arg Gln Trp Tyr
65                  70                  75                  80
```

```
Met His Leu Ser Lys Tyr Asn Val Lys Val Gly Asp Tyr Val Lys Ala
                85                  90                  95

Gly Gln Ile Ile Gly Trp Ser Gly Ser Thr Gly Tyr Ser Thr Ala Pro
            100                 105                 110

His Leu His Phe Gln Arg Met Val Asn Ser Phe Ser Asn Pro Thr Ala
            115                 120                 125

Gln Asp Pro Met Pro Phe Leu Lys Ser Ala Gly Tyr Gly Lys Ala Gly
            130                 135                 140

Gly Thr Val Thr Pro Thr Pro Asn Thr Gly Trp Lys Thr Asn Lys Tyr
145                 150                 155                 160

Gly Thr Leu Tyr Lys Ser Glu Ser Ala Ser Phe Thr Pro Asn Thr Asp
            165                 170                 175

Ile Ile Thr Arg Thr Thr Gly Pro Phe Arg Ser Met Pro Gln Ser Gly
            180                 185                 190

Val Leu Lys Ala Gly Gln Thr Ile His Tyr Asp Glu Val Met Lys Gln
            195                 200                 205

Asp Gly His Val Trp Val Gly Tyr Thr Gly Asn Ser Gly Gln Arg Ile
            210                 215                 220

Tyr Leu Pro Val Arg Thr Trp Asn Lys Ser Thr Asn Thr Leu Gly Val
225                 230                 235                 240

Leu Trp Gly Thr Ile Lys
                245

<210> SEQ ID NO 59
<211> LENGTH: 45
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (24)..(24)
<223> OTHER INFORMATION: Xaa is hydroxyproline

<400> SEQUENCE: 59

Gly Gly Tyr Gly Gly Pro Gly Pro Gly Pro Pro Gly Pro Pro Gly
1               5                   10                  15

Pro Pro Gly Pro Pro Gly Phe Xaa Gly Glu Arg Gly Pro Pro Gly Pro
            20                  25                  30

Pro Gly Pro Pro Gly Pro Pro Gly Pro Pro Gly Pro Cys
            35                  40                  45
```

LYSOSTAPHIN CONTAINING SYNTHETIC HYDROGEL CARRIERS FOR BONE REPAIR

CROSS REFERENCE TO RELATED APPLICATION

This application claims the benefit of U.S. Provisional Application 62/587,190, filed on Nov. 16, 2017, the contents of which are hereby incorporated in its entirety.

STATEMENT OF GOVERNMENT SUPPORT

This invention was made with government support under R01 AR062920 and F30 AR069472, awarded by the National Institutes of Health. The government has certain rights in this invention.

FIELD OF THE INVENTION

The invention is directed to synthetic hydrogels that are loaded with one or more therapeutic agents. The hydrogels may be contacted with an injured tissue in order to facilitate tissue healing.

BACKGROUND

Effective treatment of infected segmental bone defects and fractures remains a significant clinical challenge in the field of orthopaedics. Nonunion bone defects are a common clinical scenario accounting for over 600,000 hospital cases per year totaling over 5 billion dollars in costs. The current standard of care includes surgical placement of bone auto- and allografts to facilitate healing. However, these grafting procedures have failure rates reported as high as 13% and donor site morbidity occurs in 20-30% of cases. In the USA, nearly 112,000 orthopaedic device infections occur annually, with *Staphylococcus aureus* being the most common pathogen. These infections often lead to implant failure and subsequent removal, motivating the development of bifunctional materials that both promote repair and prevent failure due to infection. Furthermore, bacterial infection of bone grafts significantly increases implant failure rates, often leading to corrective surgery, including debridement of infected tissue, and significant morbidity to the patient. Up to 30% of nonunion injuries produce positive bacterial cultures, with staphylococcal species being the most common pathogen. This motivates the development of materials that both promote bone regeneration and prevent failure due to infection.

Lysostaphin is a metalloendopeptidase produced by *Staphylococcus simulans*. This enzyme has antimicrobial activity specific against staphylococcal species. This specificity is provided by a targeting domain that binds the *S. aureus* cell wall, and the antimicrobial activity is attributed to a catalytic domain that functions by cleaving the second and third glycine residues in the pentaglycine peptidoglycan cross bridges responsible for bacterial cell wall integrity, leading to cell lysis. The catalytic nature of lysostaphin make its antimicrobial activity independent of the bacterial metabolic state, providing activity against sessile biofilm bacteria. This activity is in contrast to most small molecule antibiotics that require metabolically active bacteria to be effective. Lysostaphin therapy prevents or reduces infection in several small animal models, including systemic infection, wound infection, endocarditis, nasal colonization, keratitis, catheter colonization, ocular infection, and neonatal infections. Biomaterial carriers have been explored to increase lysostaphin stability and retention times at the site of administration, but retention times are still limited to a few hours.

Due to the high failure rates of bone grafting to treat segmental defects, recombinant bone morphogenetic proteins (BMPs), such as BMP-2, BMP-7, and BMP-14 have been under development for use in humans. BMP-2 has been FDA approved to facilitate bone formation in anterior lumbar interbody fusion procedures, tibial fractures, and sinus augmentation procedures. However, for effective induction of bone formation, supraphysological doses are delivered, which can result in several unintended side effects such as ectopic bone formation, nerve damage, and significant inflammation. These limitations motivate the development of delivery carriers for controlled BMP-2 release to improve bone healing and reduce unintended side effects.

There remains a need for improved carriers for delivering therapeutic agents to injured and diseases tissues. There remains a need for improved implantable medical devices with reduced failure and infection rates. There remains a need for improved bone graft devices for the treatment of segmental bone injuries and defects.

SUMMARY

Disclosed herein are hydrogels that can be loaded with bone morphogenetic proteins, antibacterial agents, including antibacterial proteins, or combinations of bone morphogenetic proteins and antibacterial agents. The hydrogels can simultaneously prevent and/or treat bacterial infection, including *S. aureus* infection and repair non-healing segmental bone defects and fractures.

The details of one or more embodiments are set forth in the descriptions below. Other features, objects, and advantages will be apparent from the description and from the claims.

BRIEF DESCRIPTION OF THE FIGURES

FIG. 2A-2D depict bacterial counts reported as CFU/gel after 24 hours of culture for *S. aureus* cultures: Xen29 (FIG. 2A); *S. aureus* UAMS-1(FIG. 2B); (C) *S. aureus* 46106 (FIG. 2C); and *S. epidermidis* IDRL-8883 (2D). FIG. 2E depicts images of biofilms were grown for 24 hours and then treated overnight with a hydrogel or soluble enzyme. FIG. 2F depicts quantification of average image intensity of live bacteria after treatment as shown in FIG. 2E. Scale bar is 500μm. Means±SD. N=3-4 per group. *P<0.05, *P<0.001, **P<0.0001, one-way ANOVA with Tukey's post-hoc test.

FIG. 3A depicts a schematic diagram of mouse femur infection model. FIG. 3B-3D depict quantification of *S.*

*aureus* UAMS-1 recovered from the tissue surrounding the femur (FIG. 3B), femur bone (FIG. 3C), and stabilization needle (FIG. 3D) 7 days post-fracture. Dashed line indicates detection limit. FIG. 3E depicts histological sections of femurs 7 days post fracture stained for hematoxylin and eosin, safranin-O and fast green, and Gram. Black arrows indicate Gram-positive bacteria. Kruskal-Wallis test with Dunn's multiple comparisons test. Means±SD. N=4-8, compilation of four independent experiments. *P<0.05, **P<0.01.

FIG. 9A depicts representative μCT reconstructions at 4 and 8 weeks of UAMS-1 infected defects treated with BMP-2 loaded lysostaphin-delivering hydrogels significantly improve bone repair. FIG. 9B-9D depict quantification of bone volume from μCT imaging at 4 (FIG. 9B and FIG. 9C) and 8 (FIGS. 9D and 9E) weeks post implantation. Kruskal-Wallis test with Dunn's multiple comparisons test. Means±SD. N=12-18 per group. *P<0.05, P<0.01, *P<0.001. Defect bridging was assessed semi-quantitatively using the following scale: 0=no bone formation, 1=less than half of the defect, 2=greater than half of the defect, 3=defect bridged. Kruskal-Wallis with Dunn's multiple comparisons test. N=12-18 per group. *P<0.05, *P<0.001, **P<0.0001. Functional healing was assessed using torsion to failure testing. The average torsion to failure values for healthy mouse radii are plotted as horizontal red lines (0.0032±0.0003 Nm) as reported in Shekaran et al. Means±SD. N=8-11 per group. One-way ANOVA with Tukey's post-hoc test.

FIG. 10B depicts the principal component analysis of the array data. G-CSF (FIG. 10C); IL-1β (FIG. 10D); KC (FIG. 10E); IL-6 (FIG. 10F); MIP-1α (FIG. 10G); MIP-1β (FIG. 10H); MIP-2 (FIG. 10I); IP-10 (FIG. 10J). Cytokines with statistically different tissue levels as determined using two-way ANOVA with Bonferonni correction for multiple comparisons. Means±SD. N=6-7 per group. *P<0.05, *P<0.001, **P<0.0001, ns is not significant.

FIG. 11A depicts a hierarchical cluster analysis of cytokine profiles using the Ward Method of BMP-2 loaded lysostaphin-delivering hydrogels 4 weeks post-operatively. Segmental defects were created and hydrogel scaffolds infected with UAMS-1 with or without lysostaphin as well as sterile gels were implanted and the inflammatory response was assessed using a multiplexed cytokine array assay 4 week later. FIG. 11B depicts the principal component analysis of the array data (B). G-CSF (FIG. 11C); KC (FIG. 11D); MIP-2 (FIG. 11E); MIP-1α (FIG. 11F); MIP-1β (FIG. 11G). Cytokines with statistically different tissue levels as determined using two-way ANOVA with Bonferonni correction for multiple comparisons. Means±SD. N=6-7 per group. *P<0.05, *P<0.001, **P<0.0001, ns is not significant.

FIG. 12A-12L depicts the total number of inflammatory cells at 1 week post-implantation of BMP-2 loaded lysostaphin-delivering hydrogels. One week following segmental defect creation and implant placement, mice were euthanized and the implant and surrounding tissue were recovered and flow cytometry was performed to enumerate the total number of inflammatory cells present. Total cells (FIG. 12A), CD3+ T cells (FIG. 12B), CD3+CD4+ helper T cells (FIG. 12C), CD3+CD8+ cytotoxic T cells (FIG. 12D), CD19+ B cells (FIG. 12E), F4/80+ macrophages (FIG. 12F), CD86+ M1 macrophages (FIG. 12G), CD206+ M2 macrophages (FIG. 12H), CD11b+ myeloid cells (FIG. 12I), Ly6G+ neutrophils (FIG. 12J), Ly6C$_{low}$ AM monocytes (FIG. 12K), and Ly6C$^{high}$ IM monocytes (FIG. 12L) were enumerated. Data were log transformed and ordinary one-way ANOVA with a Tukey post hoc test was used. Means±SD. N=6-7 per group. *P<0.05, P<0.01, *P<0.001, ****P<0.0001.

FIG. 15A-15E: BMP-2 loaded lysostaphin-delivering hydrogels do not show signs of systemic toxicity. Segmental defects were created and lysostaphin-delivering hydrogels loaded were BMP-2 with and without infection were implanted. Systemic toxicity was assessed at 1 week with liver function testing. Serum samples were tested for total protein (FIG. 15A), albumin (FIG. 15B), aspartate aminotransferase (AST) (FIG. 15C), alanine aminotransferase (ALT) (FIG. 15D), and alkaline phosphatase (Alk phosphatase) (FIG. 15E) levels. Means±SD. N=5-6 per group. One-way ANOVA with Tukey's post-hoc test. No differences were detected between groups.

FIG. 23A depicts μCT reconstructions of the fracture callus 5-weeks post-operation. FIG. 23B depicts quantification of fracture callus volume and at 5 weeks. FIG. 23C depicts mechanical integrity of femurs as assessed by ex vivo torsion to failure testing. FIG. 23D depicts hematoxylin and eosin and safranin-O and fast green staining of femurs. N=6 per group. *$P<0.05$, Student's t test.

DETAILED DESCRIPTION

Figure 1A:
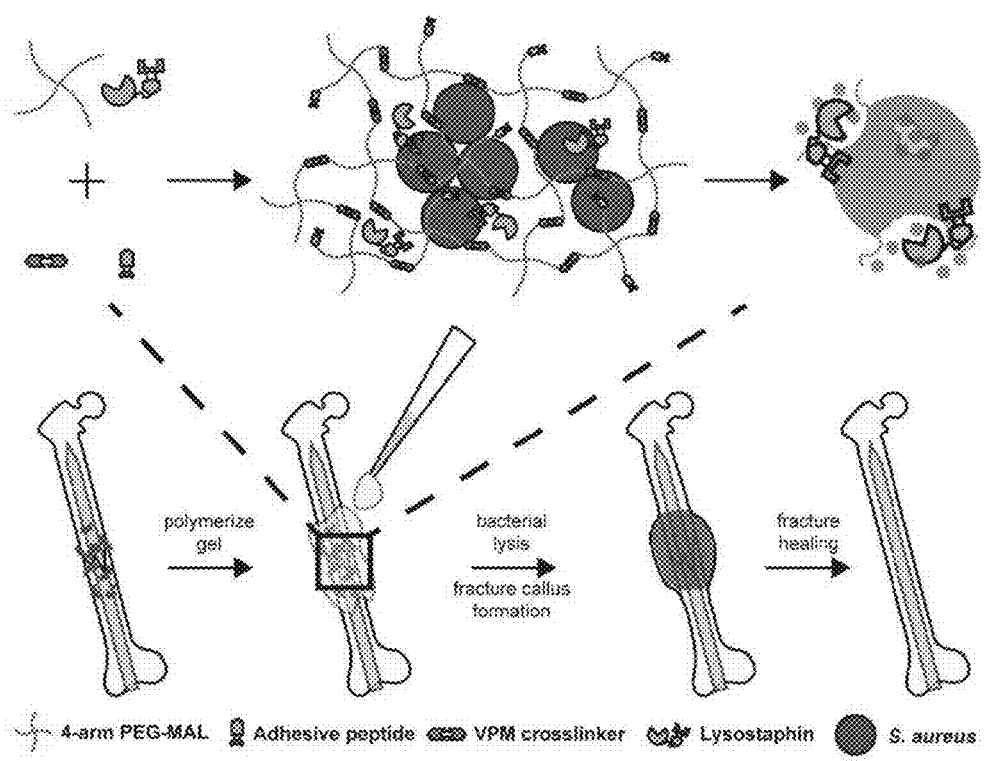
FIG. 1A depicts a schematic diagram of lysostaphin encapsulation within protease degradable PEG-MAL hydrogel and subsequent application to infected femurs, which leads to fracture callus formation and healing.
Figure 1B:
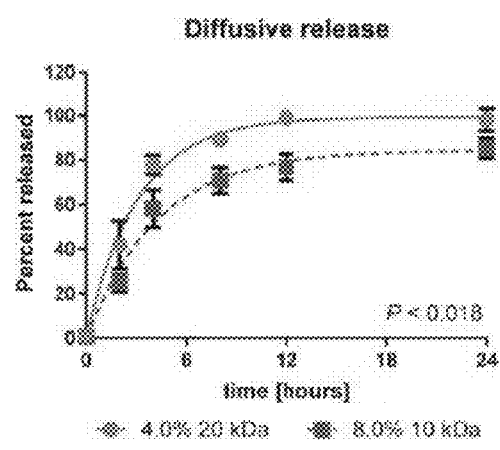
FIG. 1B depicts lysostaphin release from synthetic hydrogels with one-phase association fit with extra sum of squares F test to compare K values are different.
Figure 1C:
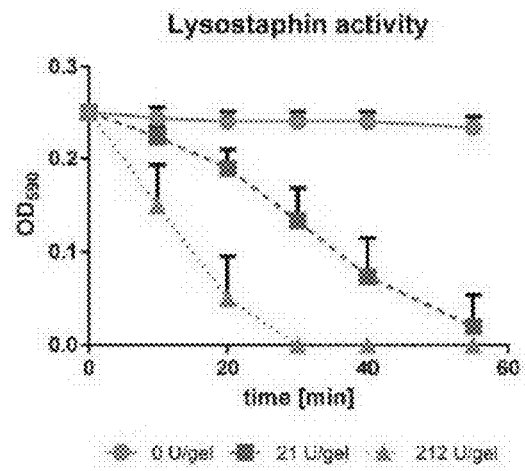
FIG. 1C depicts optical density curves of lysostaphin-laden hydrogels placed in *S. aureus* UAMS-1 suspensions as a function of incubation time.
Figure 1D:
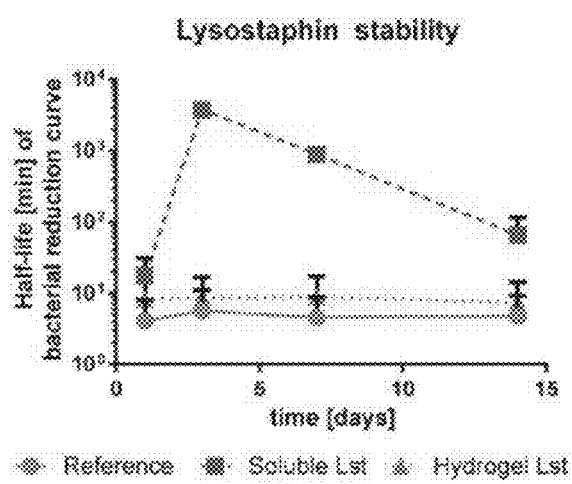
FIG. 1D depicts lysostaphin activity as measured by the average half-life of the kinetic bacteria reduction assay at 1, 3, 7, and 14 days after hydrogel polymerization.
Figure 1E:
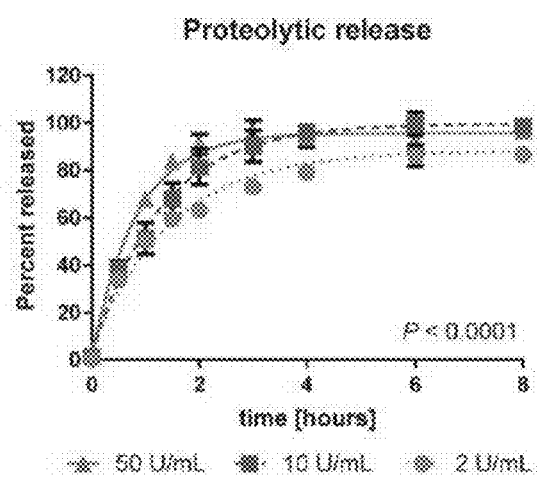
FIG. 1E depicts protease-triggered release of lysostaphin with one-phase association fit using extra sum of squares F test to compare all K values are different. Means±SD. N=3-5.
Figure 4A:
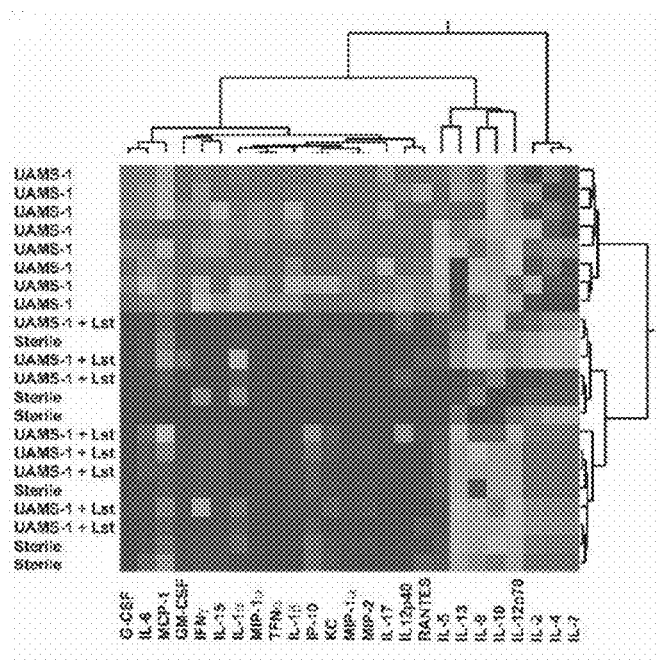
FIG. 4A depicts a hierarchical cluster analysis of cytokine profiles of lysostaphin-laden hydrogel therapy in a sterile inflammatory environment. Femora were fractured and infected with UAMS-1 and treated with hydrogels with or without lysostaphin and the inflammatory milieu of tissue at the fracture site 7 days post-infection was assessed using multiplexed cytokine analysis.
Figure 4B:
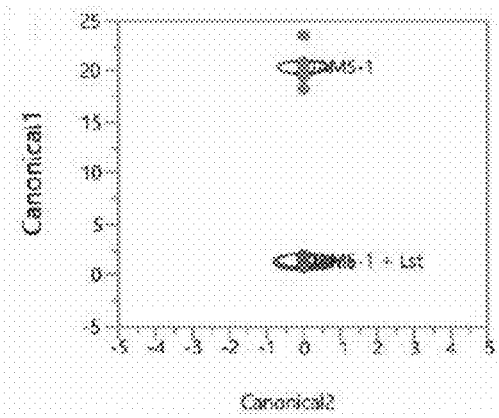
FIG. 4B depicts a multivariate-ANOVA plot using a sum combination across cytokines, P<0.001.
Figure 4C:
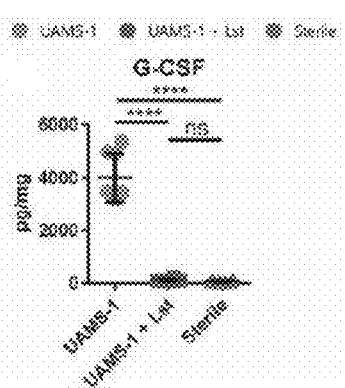
FIG. 4C-4K depict cytokines concentration with statistically different tissue levels as determined using two-way ANOVA with a Bonferonni Correction for multiple comparisons. G-CSF (FIG. 4C); IL-1α (FIG. 4D); IL-1β (FIG. 4E); IL-6 (FIG. 4F); KC (FIG. 4G); IP-10 (FIG. 4H); MIP-1α (FIG. 4I); MIP-1β (FIG. 4J); MIP-2 (FIG. 4K). Means±SD. N=6-8 per group. *P<0.05, *P<0.001, **P<0.0001, ns is not significant.
Figure 4D:
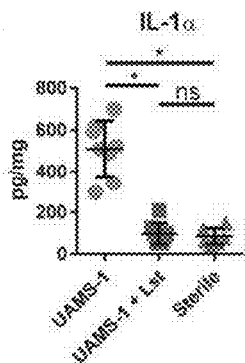
Figure 4E:
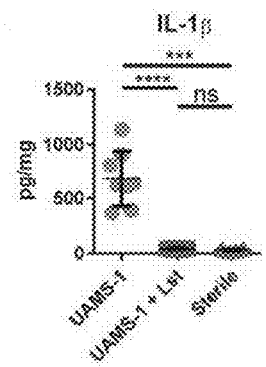
Figure 4F:
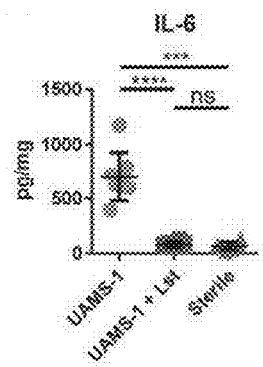
Figure 4G:
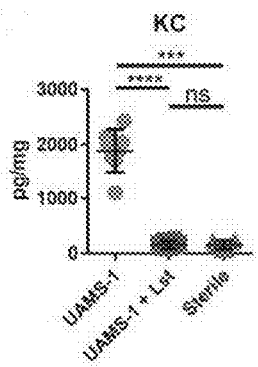
Figure 4H:
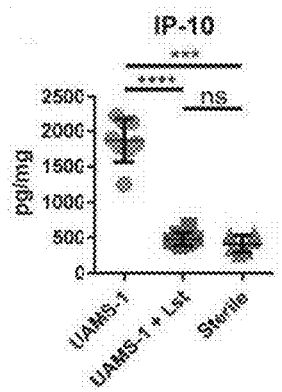
Figure 4I:
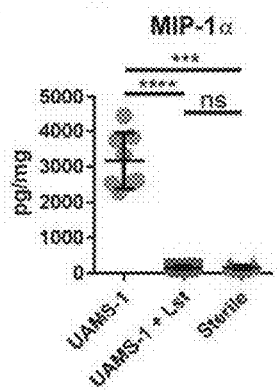
Figure 4J:
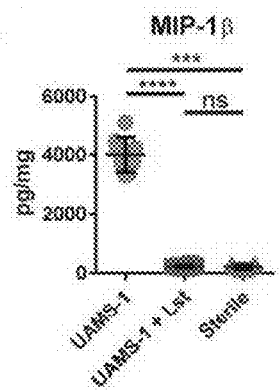
Figure 4K:
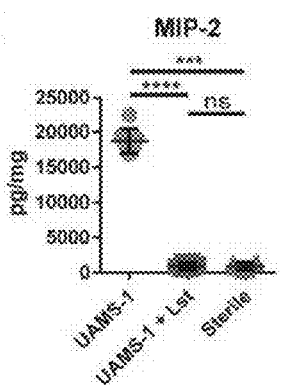
Figure 5A:
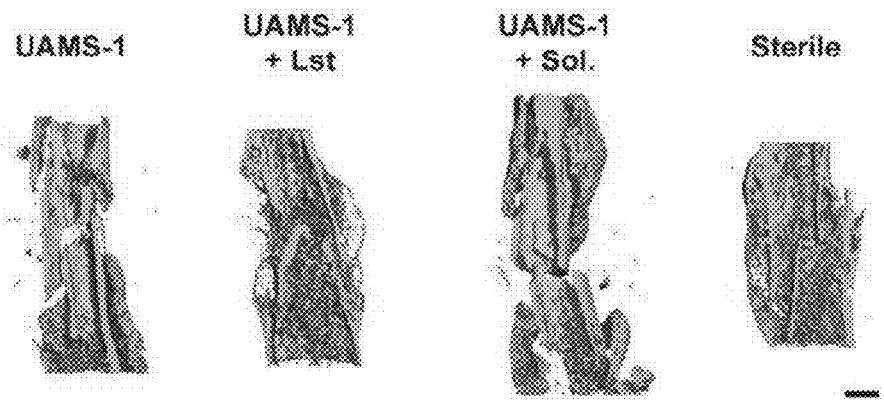
FIG. 5A depicts μCT reconstructions of the fracture callus 5 weeks post-operation (scale bar 1 mm).
Figure 5B:
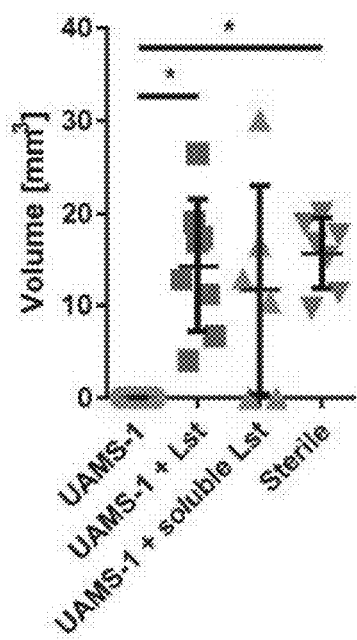
FIG. 5B-5C depict quantification of μCT reconstructions showing the fracture callus volume (FIG. 5B) and bone volume (FIG. 5C) within the fracture callus at 5 weeks.
Figure 5C:
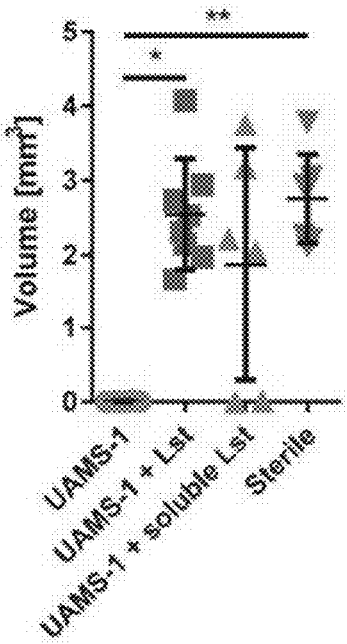
Figure 5D:
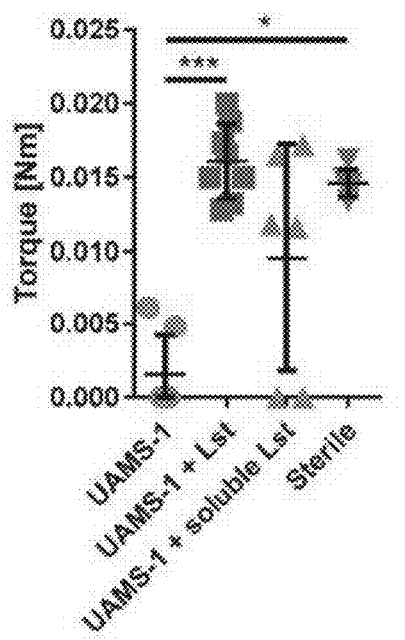
FIG. 5D depicts mechanical strength of femurs as assessed by ex vivo torsion to failure testing.
Figure 5E:
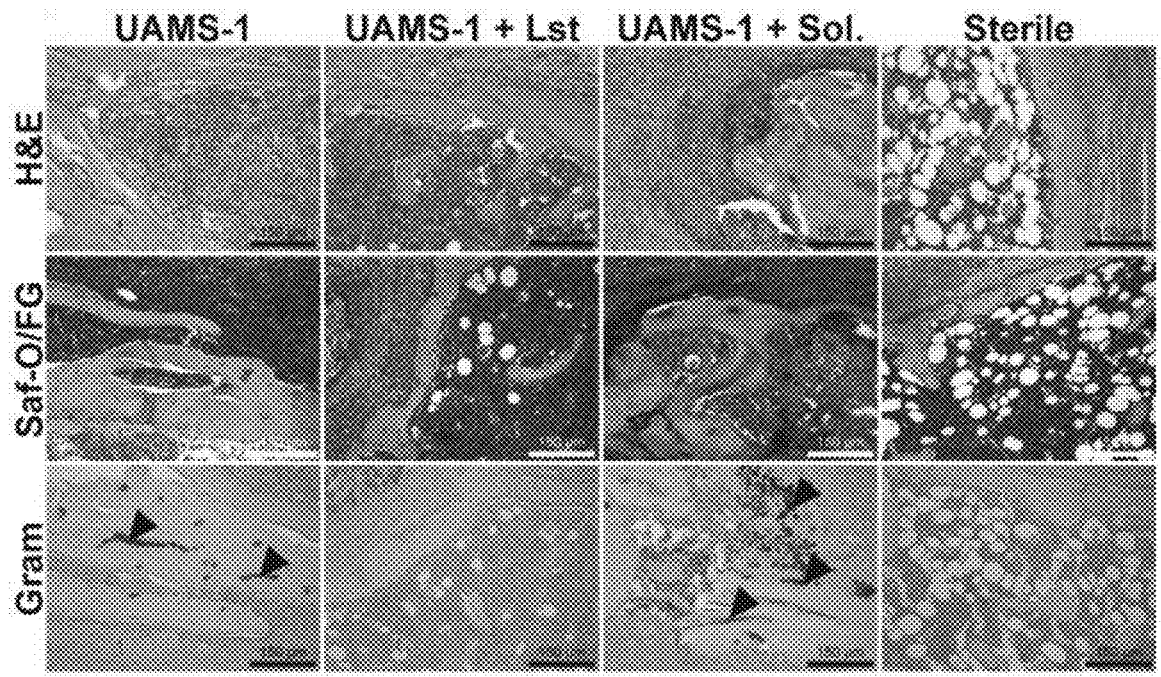
FIG. 5E depicts hematoxylin and eosin, safranin-O and fast green, and Gram staining of femurs. Black arrows indicate Gram-positive bacteria. Kruskal-Wallis test with Dunn's multiple comparisons test. Means±SD. N=6-8, compilation of two individual experiments. *P<0.05, P<0.01, *P<0.001.
Figure 6A:
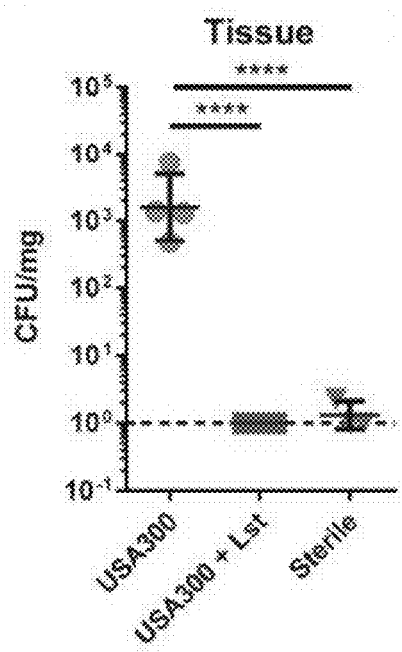
FIG. 6A-C depict a quantification of MRSA USA300 recovered from the tissue surrounding the femur (FIG. 6A), femur (FIG. 6B), and stabilization needle (FIG. 6C) at 7 days post-fracture. Dashed line indicates detection limit. ANOVA with Tukey post-hoc test for (A) and (B). Kruskal-Wallis test with Dunn's multiple comparisons test for (C) Means±SD. N=3-4. *P<0.05, ****P<0.0001.
Figure 6B:
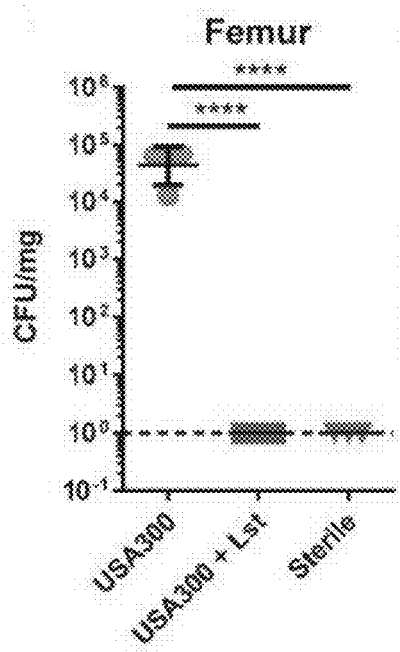
Figure 6C:
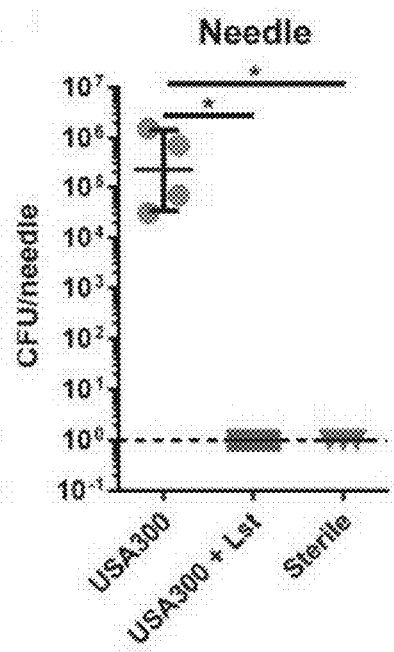
Figure 7:
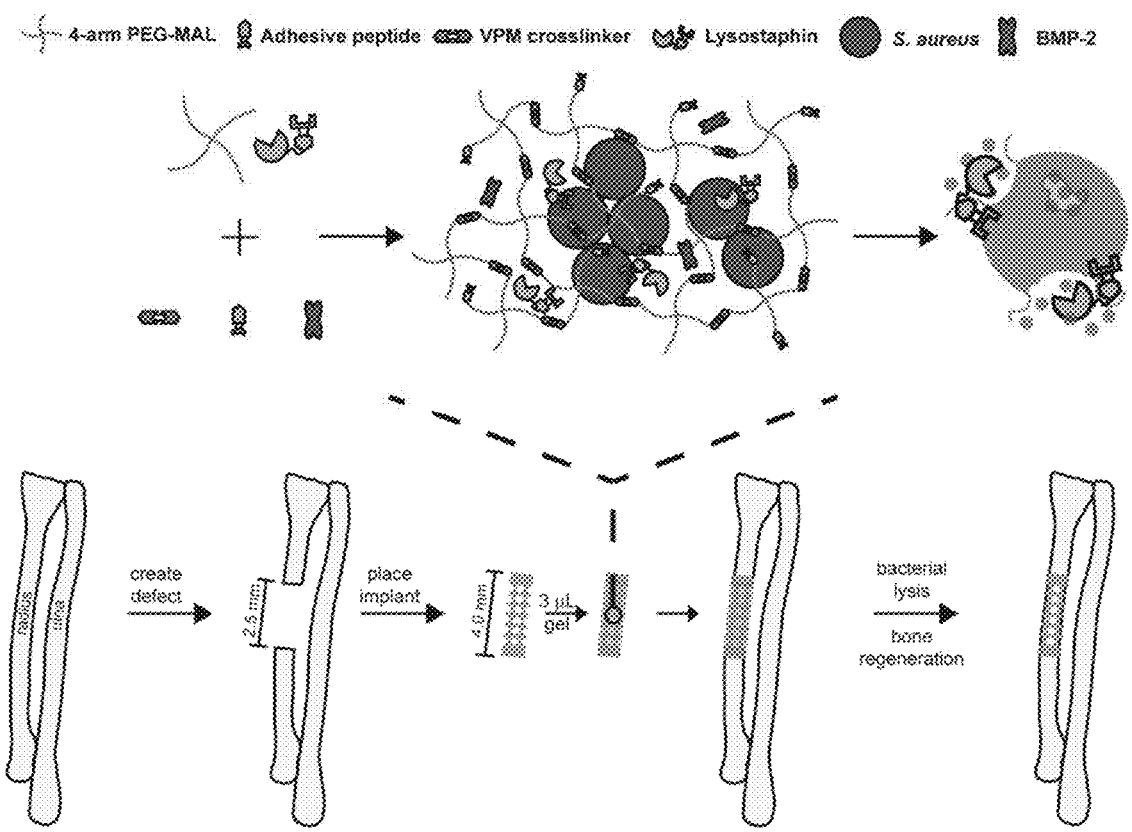
FIG. 7 depicts lysostaphin and BMP-2 co-delivery to a critical-size segmental bone defect. A 2.5 mm segment of the radius is removed to create a critical-sized bone defect that does not spontaneously heal. A PEG-4MAL hydrogel functionalized with the adhesive ligand GFOGER and loaded with lysostaphin and BMP-2 is synthesized with *S. aureus*. Lysostaphin enzymatically creates holes in the bacterial cell wall leading to lysis. These infected hydrogel scaffolds are loaded into a 4 mm polyimide sleeve and placed over the ends of the defect. Co-delivery of BMP-2 and lysostaphin results in infection clearance followed by subsequent defect regeneration.
Figure 8:
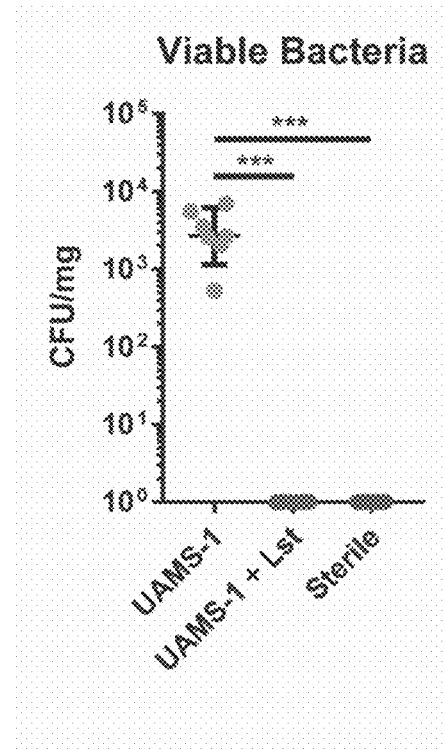
FIG. 8 depicts how lysostaphin-delivering hydrogels eliminate infection at 8 weeks. Viable bacteria recovered from UAMS-1 infected radial defects 8 weeks post-implantation. Kruskal-Wallis test with Dunn's multiple comparisons test. Means±SD. N=7-8 per group. *** P<0.001.
Figure 9F:
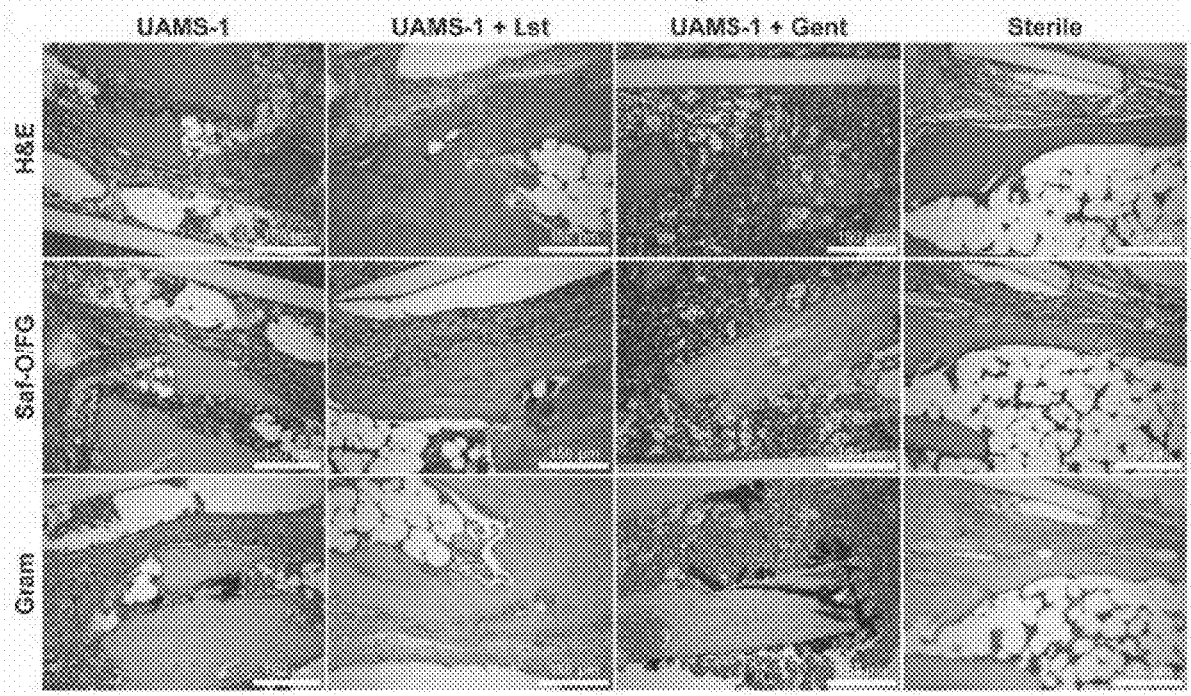
FIG. 9F depicts mouse radii that were sectioned and stained with hematoxylin & eosin (H&E), safranin-O/fast green (Saf-O/FG), and Gram stain. One sample was randomly selected and prepared per experimental group. Representative images are displayed.
Figure 10A:
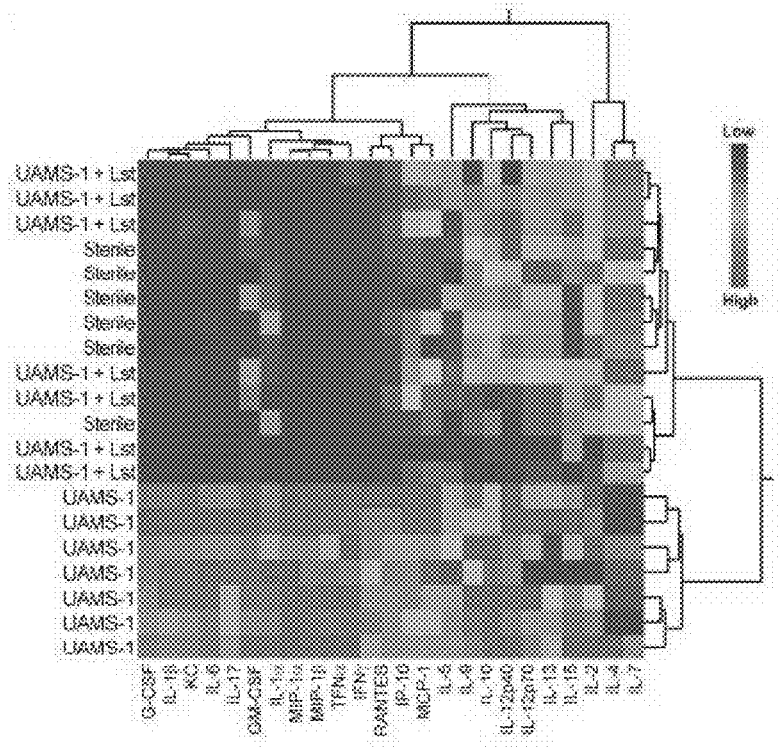
FIG. 10A depicts a hierarchical cluster analysis of cytokine profiles using the Ward Method showing how BMP-2 loaded lysostaphin-delivering hydrogels restore the local inflammatory environment to a regenerative state one week after implantation. Segmental defects were created and hydrogel scaffolds infected with UAMS-1 with or without lysostaphin as well as sterile gels were implanted and the inflammatory response was assessed using a multiplexed cytokine array assay 1 week later.
Figures 12I, 12J, 12K, 12L:
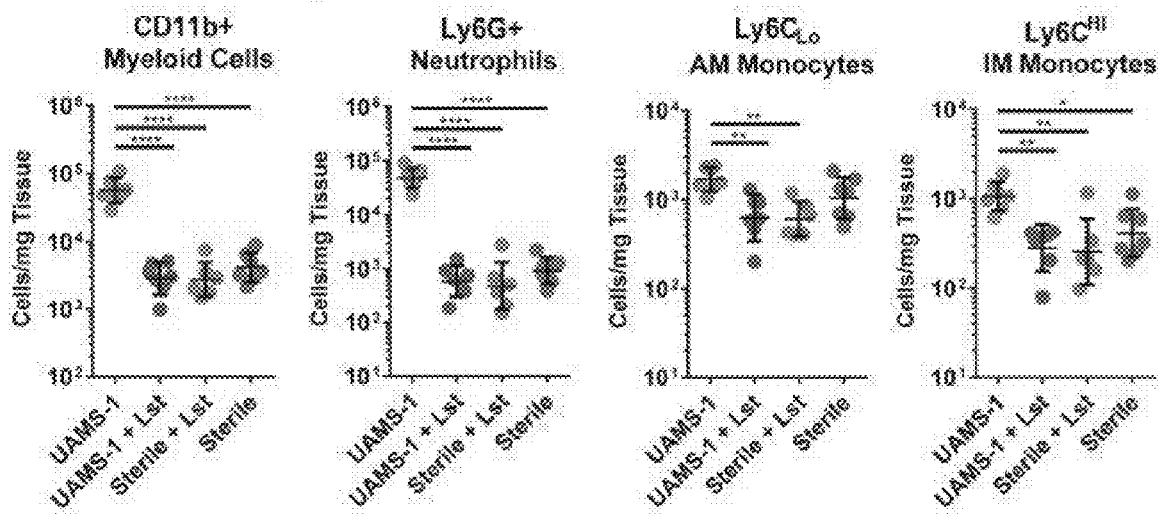
Figures 13A, 13B, 13C, 13D:
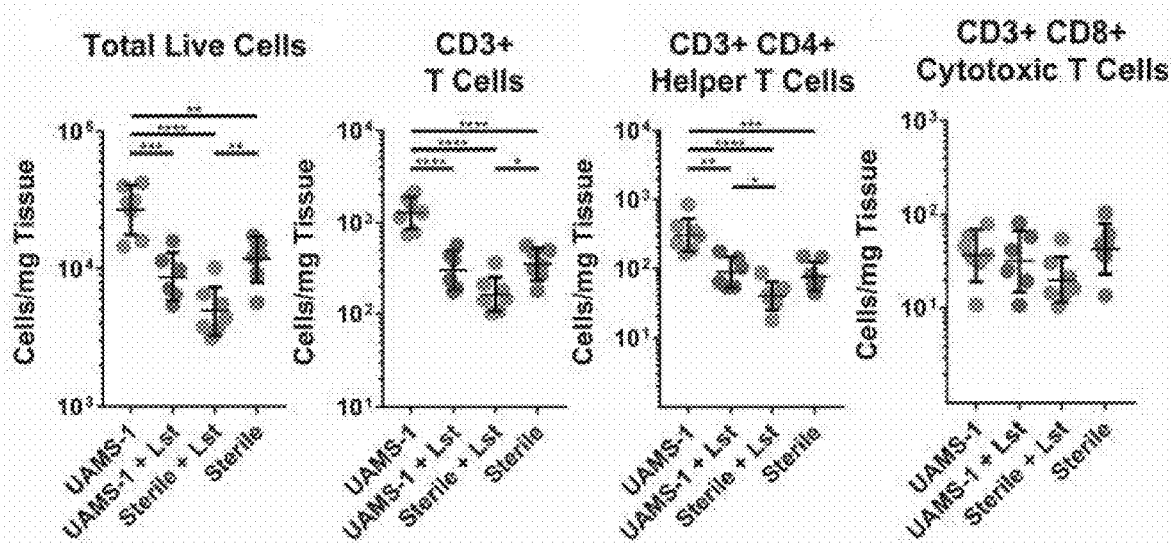
FIG. 13A-13L depict the total number of inflammatory cells at 4 weeks post-implantation of BMP-2 loaded lysostaphin-delivering hydrogels. Four weeks following segmental defect creation and implant placement, mice were euthanized and the implant and surrounding tissue were recovered and flow cytometry was performed to enumerate the total number of inflammatory cells present. Total cells (FIG. 13A), CD3+ T cells (FIG. 13B), CD3+CD4+ helper T cells (FIG. 13C), CD3+CD8+ cytotoxic T cells (FIG. 13D), CD19+ B cells (FIG. 13E), F4/80+ macrophages (FIG. 13F), CD86+ M1 macrophages (FIG. 13G), CD206+ M2 macrophages (FIG. 13H), CD11b+ myeloid cells (FIG. 13I), Ly6G+ neutrophils (FIG. 13J), $Ly6C_{low}$ AM monocytes (FIG. 13K), and $Ly6C^{high}$ IM monocytes (FIG. 13L) were enumerated. Data were log transformed and ordinary one-way ANOVA with a Tukey post hoc test was used. Means±SD. N=6-7 per group. *$P<0.05$, $P<0.01$, *$P<0.001$, ****$P<0.0001$.
Figure 13E:
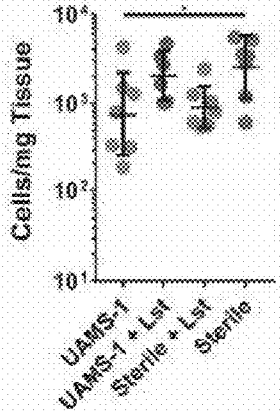
Figure 13F:
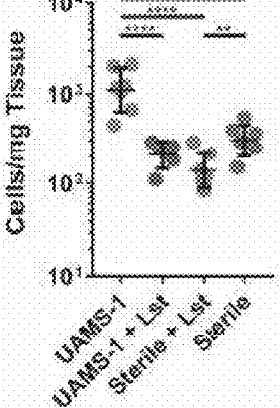
Figure 13G:
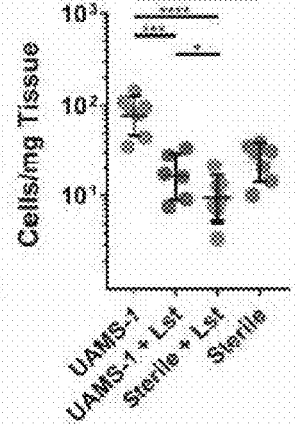
Figure 13H:
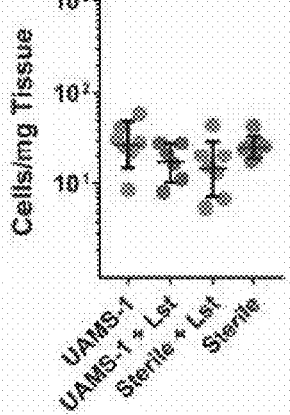
Figure 13I:
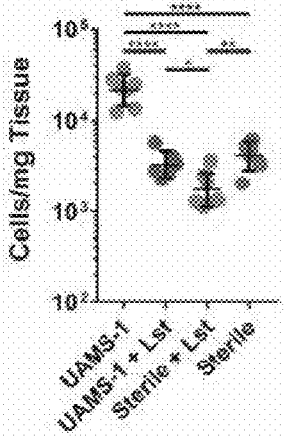
Figure 13J:
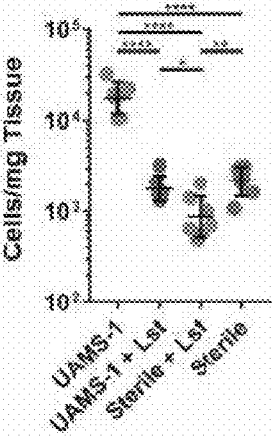
Figure 13K:
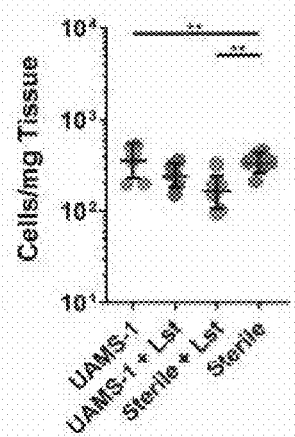
Figure 13L:
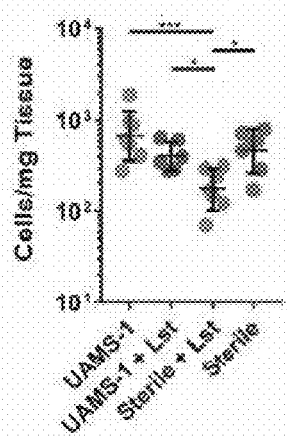
Figure 14A:
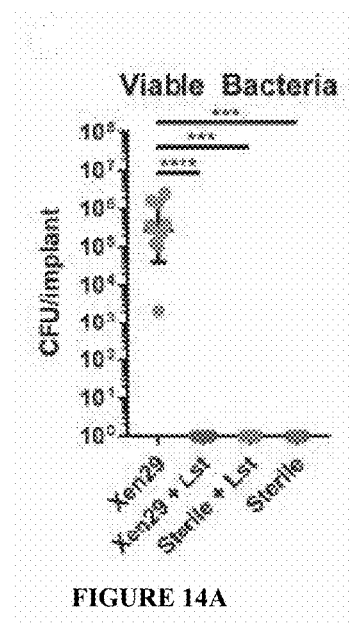
FIG. 14A depicts the number of viable bacteria recovered from the implant and surrounding tissue one week after implantation.
Figure 14B:
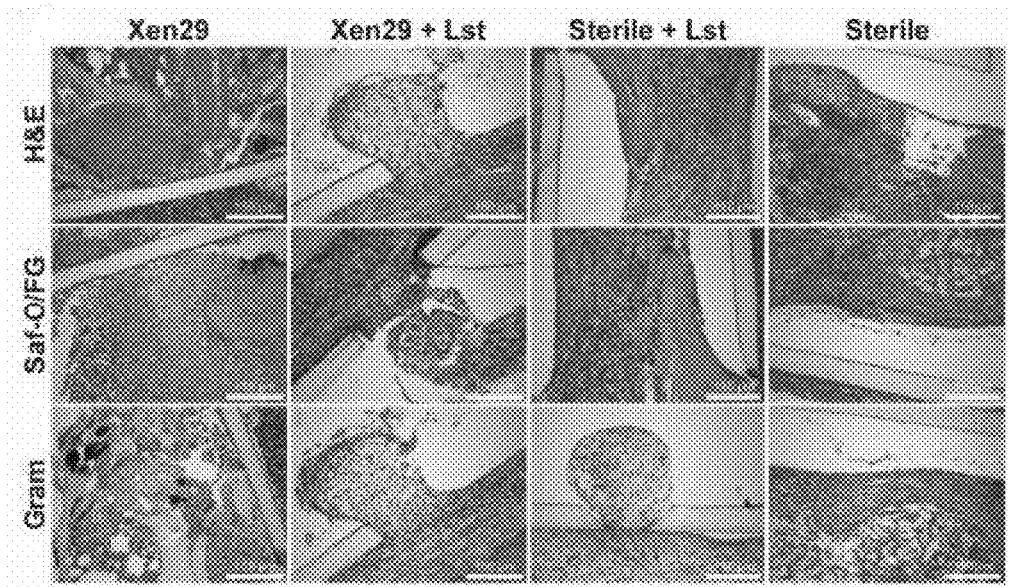
FIG. 14B depicts histologic images of tissue sections stained with hematoxylin & eosin (H&E), safranin-O/fast green (Saf-O/FG), and G ram stain. Kruskal-Wallis test with Dunn's multiple comparisons test. Meas±SD. N=5-11 per group. * $P<0.001$; ** $P<0.0001$.
Figure 16:
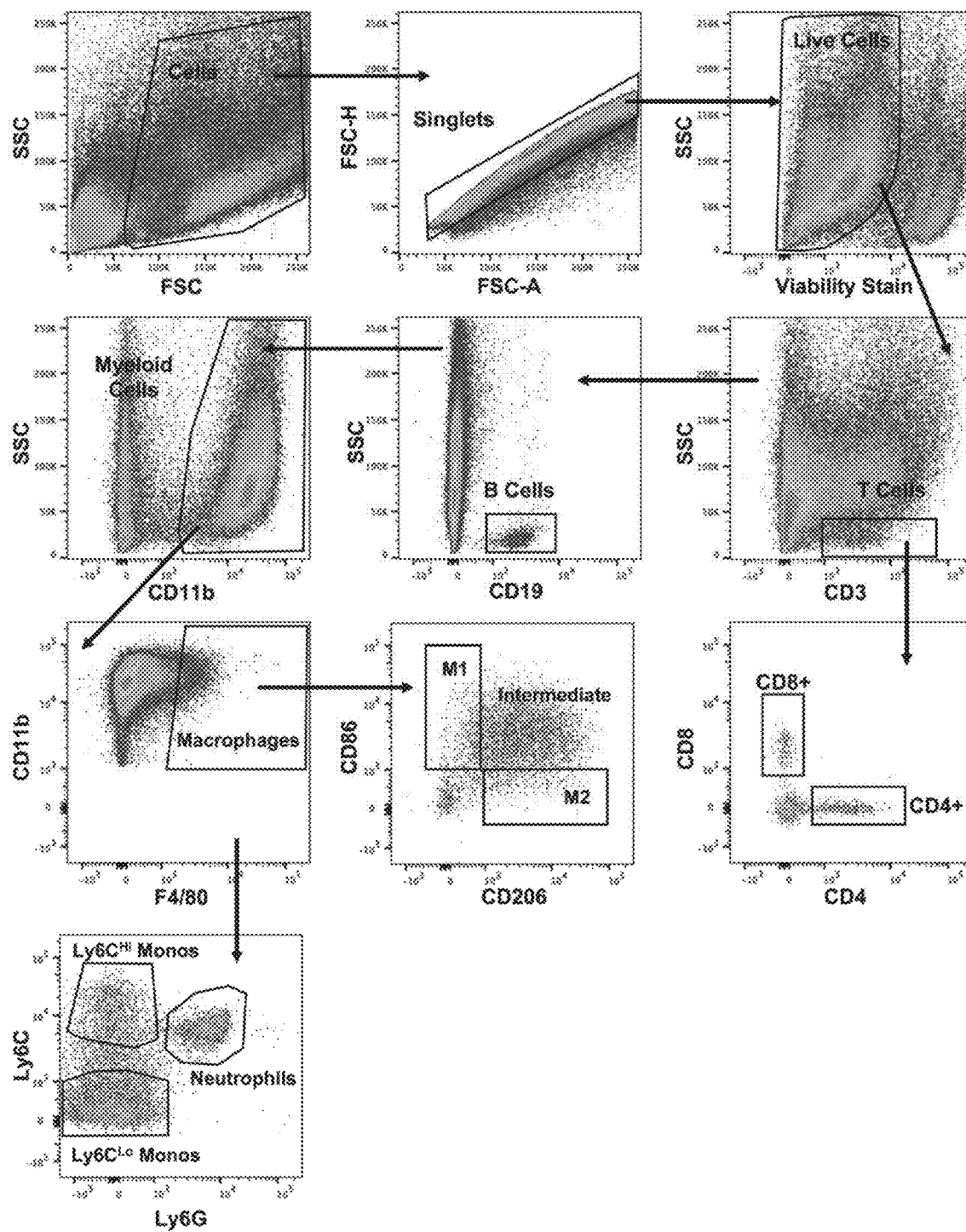
FIG. 16 depicts a gating strategy for inflammatory cell profiling analysis. Single cell suspension of tissue samples were created and stained for subsequent flow cytometry analysis. Single cells were identified and live cells were selected. T cells were identified by selecting as low side scatter CD3 positive events and then sorted into CD8 positive cytotoxic T cells and CD4 positive helper T cells. B cells were low side scatter CD19 positive events. Myeloid cells were identified as being CD11b positive. Macrophages were identified as CD11b and F4/80 positive events then split into CD86 positive M1 and CD206 positive M2 subsets. Neutrophils are identified as Ly6G positive myeloid cells. Monocytes are classified as Ly6G negative myeloid cells and split into Ly6CHi IM monocytes and Ly6CLo AM monocytes.
Figure 17A:
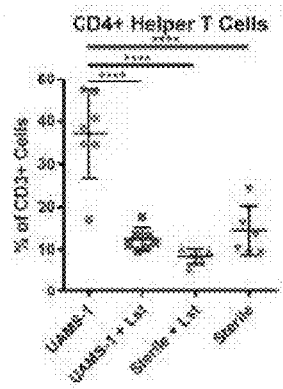
FIG. 17A-17H depicts the percent of parent inflammatory cells at 1 week post-implantation of BMP-2 loaded lysostaphin-delivering hydrogels. One week following segmental defect creation and implant placement, mice were euthanized and the implant and surrounding tissue were recovered and flow cytometry was performed to enumerate the total number of inflammatory cells present. CD4+ helper T cells as a percent of CD3+ cells (FIG. 17A), CD8+ cytotoxic T cells as a percent of CD3+ cells (FIG. 17B), F480+ macrophages as a percent of CD11b+ cells (FIG. 17C, CD86+ M1 macrophages as a percent of F480+ cells (FIG. 17D), CD206+ M2 macrophages as a percent of F4/80+ cells (FIG. 17E), Ly6G+ neutrophils as a percent of CD11b+ cells (FIG. 17F), Ly6CLo AM monocytes as a percent of CD11b+ cells (FIG. 17G), and $Ly6C^{Hi}$ IM monocytes as a percent of CD11b+ cells (FIG. 17H) were analyzed. Ordinary one-way ANOVA with a Tukey post hoc test, or Kurskall-Wallis with Dunn's test for non-parametric data was used. Means±SD. N=6-7 per group. *$P<0.001$, **$P<0.0001$.
Figure 17B:
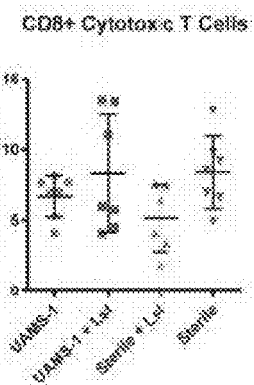
Figure 17C:
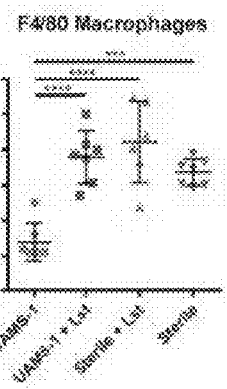
Figure 17D:
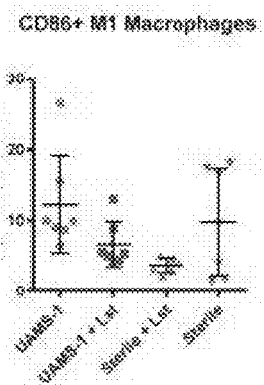
Figure 17E:
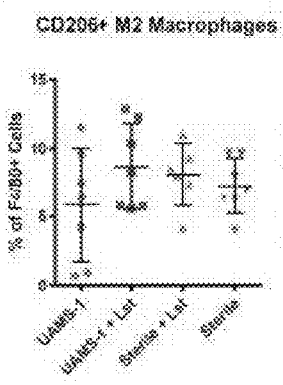
Figure 17F:
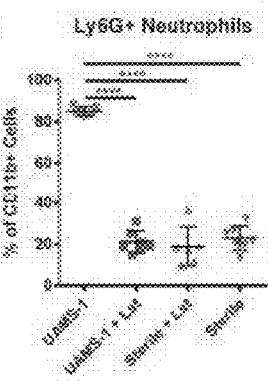
Figure 17G:
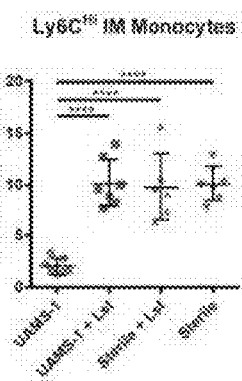
Figure 17H:
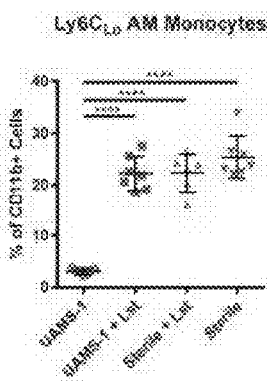
Figure 18A:
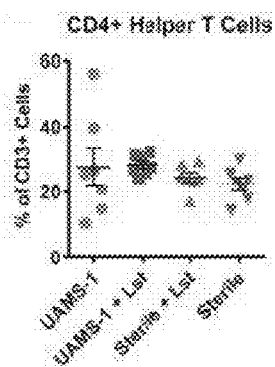
FIG. 18A-18H depicts the ercent of parent inflammatory cells at 4 weeks post-implantation of BMP-2 loaded lysostaphin-delivering hydrogels. Four weeks following segmental defect creation and implant placement, mice were euthanized and the implant and surrounding tissue were recovered and flow cytometry was performed to enumerate the total number of inflammatory cells present. CD4+ helper T cells as a percent of CD3+ cells (FIG. 18A), CD8+ cytotoxic T cells as a percent of CD3+ cells (FIG. 18B), F480+ macrophages as a percent of CD11b+ cells (FIG. 18C), CD86+ M1 macrophages as a percent of F480+ cells (FIG. 18D), CD206+ M2 macrophages as a percent of F4/80+ cells (FIG. 18E), Ly6G+ neutrophils as a percent of CD11b+ cells (FIG. 18F), Ly6CLo AM monocytes as a percent of CD11b+ cells (FIG. 18G), and $Ly6C^{Hi}$ IM monocytes as a percent of CD11b+ cells (FIG. 18H) were analyzed. Ordinary one-way ANOVA with a Tukey post hoc test, or Kurskall-Wallis with Dunn's test for non-parametric data was used. Means±SD. N=7 per group. *$P<0.05$, *$P<0.001$, **$P<0.0001$.
Figure 18B:
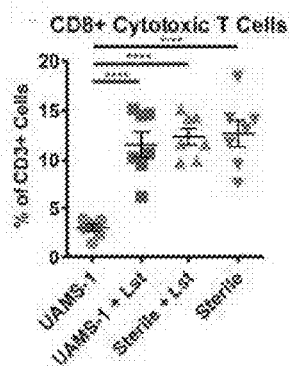
Figure 18C:
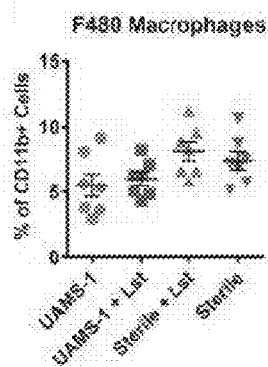
Figure 18D:
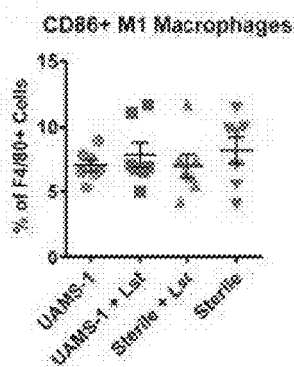
Figure 18E:
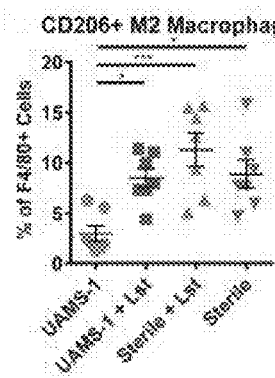
Figure 18F:
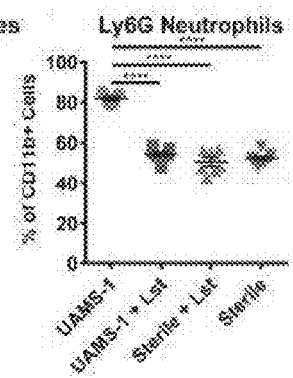
Figure 18G:
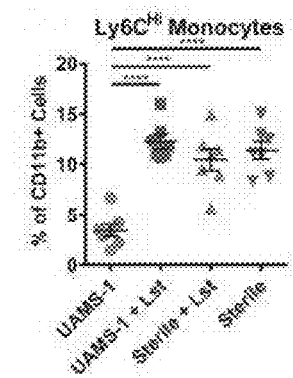
Figure 18H:
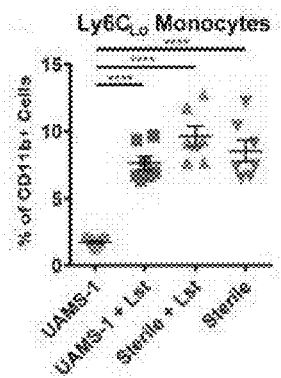
Figure 19:
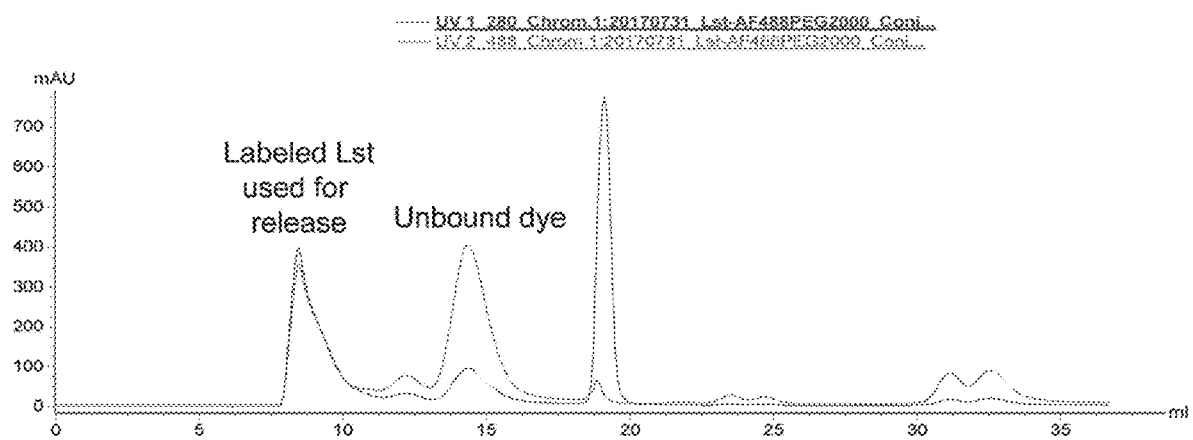
FIG. 19 depicts fluorescent lysostaphin labeling and purification. Lysostaphin was labeled with an AlexaFluor 488 fluorescent dye conjugated to a 2000 Da PEG chain functionalized with an NETS-ester to label free-amines and purified with size exclusion chromatography. During the elution phase, 280 nm light was used to monitor protein content (blue) and 488 nm light monitored dye fluorescence (red). The peak with both 280 nm and 488 nm components was collected and used for the release studies.
Figure 20A:
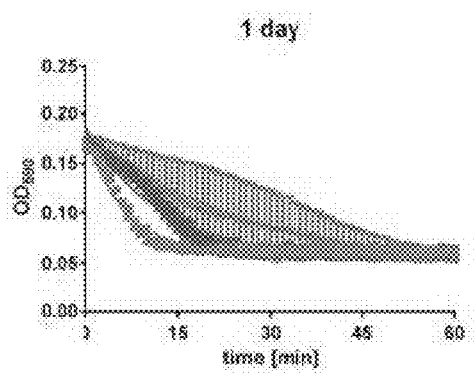
FIG. 20A-20D depict kinetic optical density plots of UAMS-1 reduction from degraded hydrogels. Hydrogels and soluble lysostaphin were degraded in protease and the sample was added to a bacterial suspension of UAMS-1. The optical density of the suspension was monitored for one hour after one day (FIG. 20A), three days (FIG. 20B), seven days, (FIG. 20C) and fourteen days (FIG. 20D) at 25° C. Solid line represents one-phase decay line of best fit. Means±SD. N=3-5.
Figure 20B:
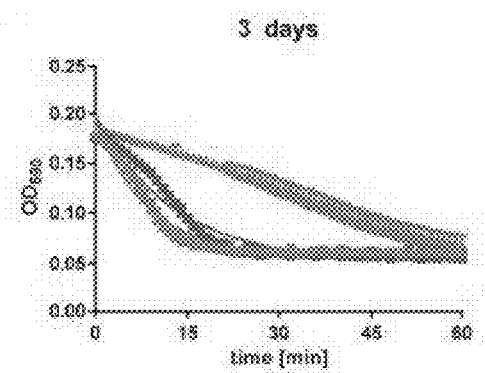
Figure 20C:
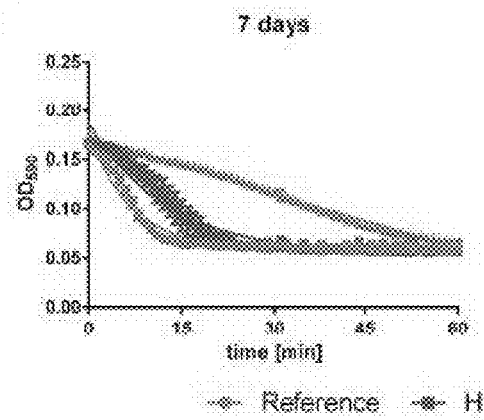
Figure 20D:
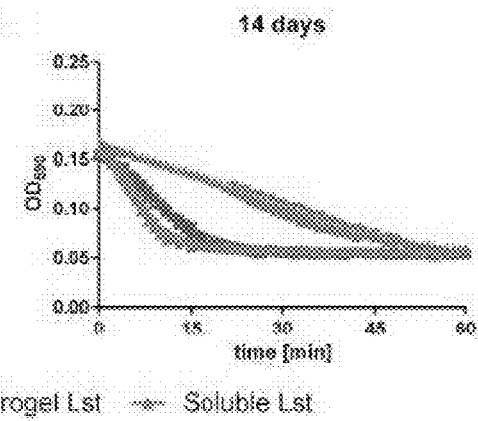
Figure 21A:
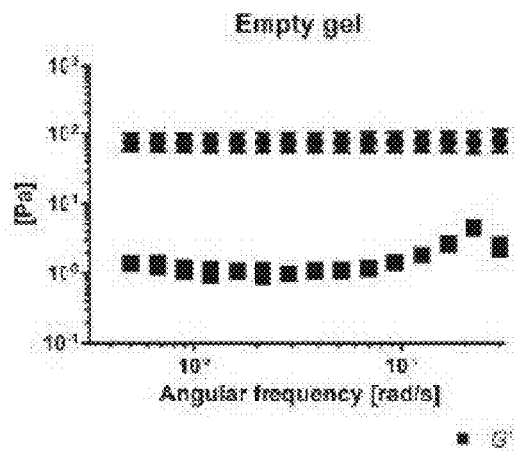
FIG. 21A-D depict mechanical properties of lysostaphin-delivering hydrogels. Angular frequency sweep of (A) empty (FIG. 21A) and lysostaphin-delivering (FIG. 21B) hydrogels at a constant strain of 2%. Average storage (FIG. 21C) and loss modulus (FIG. 21D) of empty and lysostaphin-delivering hydrogels of eight data points within the linear region of the angular frequency sweep of each sample. Student t test. Means±SD. N=7.
Figure 21B:
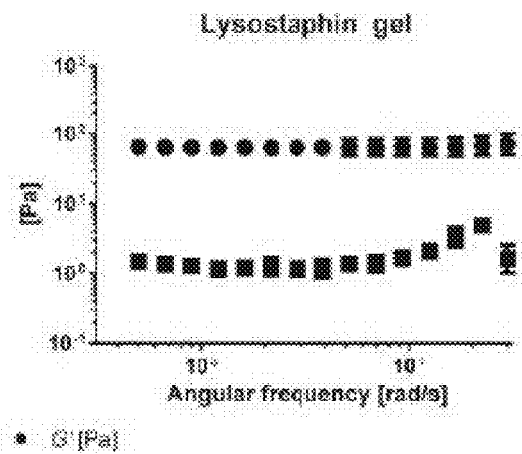
Figure 21C:
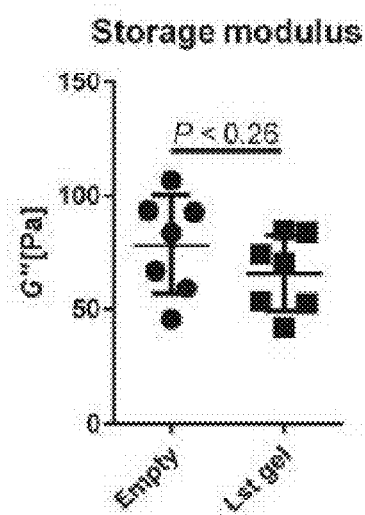
Figure 21D:
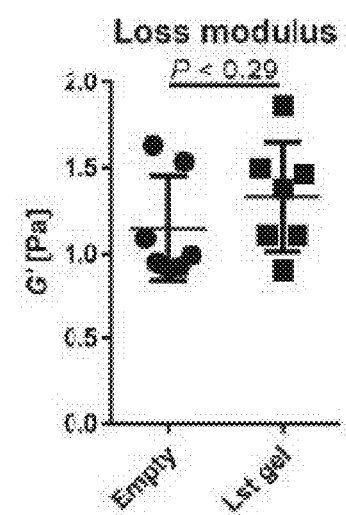
Figures 22A, 22B:
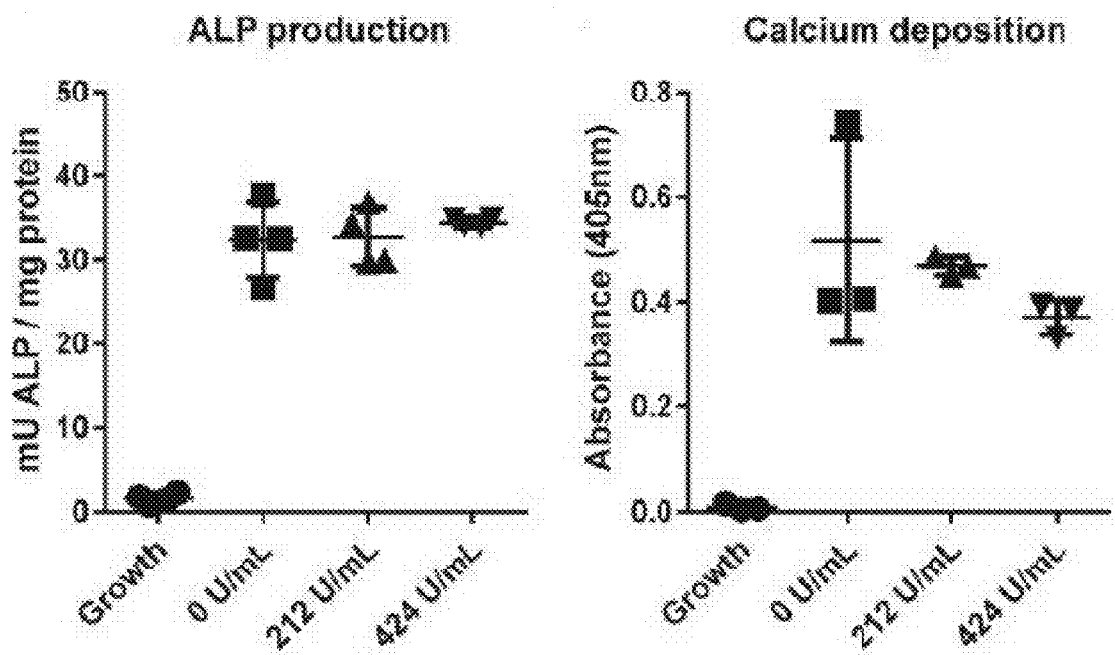
FIG. 22A depicts alkaline phosphatase production of hMSC exposed to lysostaphin after 9 days in culture.
FIG. 22B depicts quantification of calcium deposition by Alizarin Red extraction from hMSC after 21 days in culture.
Figure 22C:
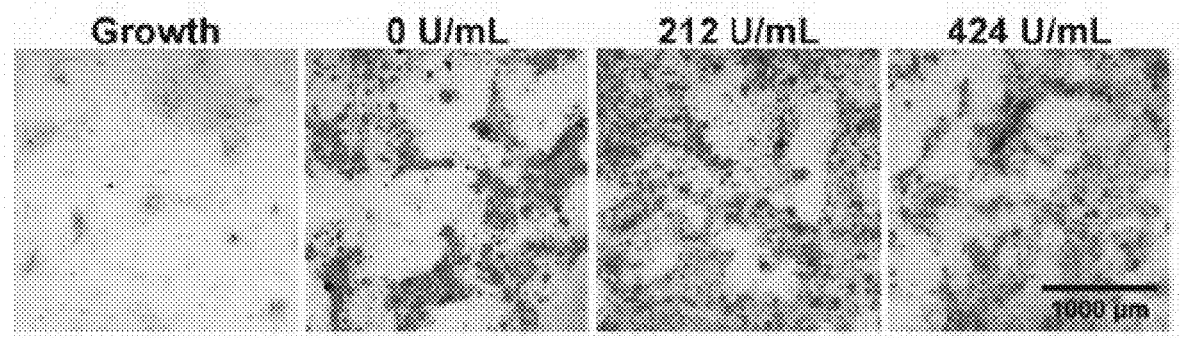
FIG. 22C depicts representative images of Alizarin Red staining of hMSC cultures. One-way ANOVA with Tukey's post-hoc test. Means±SD. N=3-4. All comparisons not significant.
Figure 24A:
FIG. 24A-24B depict μCT reconstructions of non-healing and healing soluble lysostaphin treated fractures. Mice treated with soluble lysostaphin exhibited a non-healing (FIG. 24A) and healing (FIG. 24B) response.
Figure 24B:
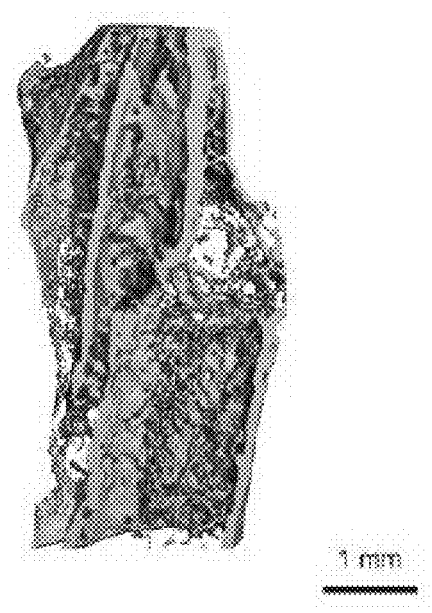

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes—from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

Disclosed herein are synthetic hydrogels capable of treating and preventing bacterial infection, as well as supporting bone regrowth and repair. The synthetic hydrogel can be used as a vehicle for the administration of medicaments such as antibiotics and therapeutic proteins to a patient in need thereof.

In some embodiments, the hydrogels disclosed herein can contain one or more antibacterial agents. Suitable antibacterial agents include antibacterial proteins—one such agent is lysostaphin, including variants thereof. Lysostaphin is an endopeptidase capable of specifically cleaving the cross-linking pentaglycine bridges in the cell walls of staphylococci. Because the cell wall bridges of S. aureus contain a high proportion of pentaglycine, lysostaphin is highly effective in lysing S. aureus, although activity against other species of staphylococci has been demonstrated. Moreover, lysostaphin does not require active bacterial growth to elicit its antibacterial effects. The term "lysostaphin," as used herein, encompasses any enzyme or anti-staphylococcal agent having proteolytic activity, in vitro and in vivo, against glycine-containing bridges in the cell wall peptidoglycan of staphylococci. The compositions of the invention are therefore applicable against any bacteria susceptible to attack by lysostaphin activity. Lysostaphins within the scope of the invention encompass: wild-type lysostaphin and related proteins or anti-staphylococcal agents, lysostaphin mutants, variants, fully synthetic and partially synthetic lysostaphins, human or animal lysostaphins, and recombinantly expressed lysostaphin proteins. Lysostaphin variants may be generated by post-translational processing of the protein (either by enzymes present in a producer strain or by means of enzymes or reagents introduced at any stage of the process) or by mutation of the structural gene. Mutations may include site-deletion, insertion, point mutations, domain removal and replacement mutations. Lysostaphin includes, for example, lysostaphin purified from *S. simulans*, Ambicin L (recombinant lysostaphin produced in *Bacillus sphaericus*), and mature lysostaphin purified from a *Lactococcus lactis* expression system or an *E. coli* expression system, and truncated lysostaphin. In some instance, the lysostaphin can have the wild-type sequence:

(SEQ ID. 58)
AATHEHSAQWLNNYKKGYGYGPYPLGINGGMHYGVDFFMNIGTPVKAISS

GKIVEAGWSNYGGGNQIGLIENDGVHRQWYMHLSKYNVKVGDYVKAGQII

GWSGSTGYSTAPHLHFQRMVNSFSNPTAQDPMPFLKSAGYGKAGGTVTPT

PNTGWKTNKYGTLYKSESASFTPNTDIITRTTGPFRSMPQSGVLKAGQTI

HYDEVMKQDGHVWVGYTGNSGQRIYLPVRTWNKSTNTLGVLWGTIK.

In some embodiments, a lysostaphin variant can be employed, for instance a lysostaphin variant can a single amino acid substitution (e.g., any one of the amino acid substitutions described herein) when compared with the wild-type sequence, i.e., lysostaphin V-1; a lysostaphin variant can have two amino acid substitutions when compared with the wild-type sequence i.e., lysostaphin V-2. In other embodiments, a lysostaphin variant can have three amino acid substitutions when compared with the wild-type sequence i.e., lysostaphin V-3. In further embodiments, a lysostaphin variant can have four or more amino acid substitutions when compared with the wild-type sequence i.e., lysostaphin V-4+. In some embodiments, the lysostaphin can have an amino acid sequence that is at least 60%, more preferably at least 70%, more preferably at least 80%, more preferably 90%, more preferably at least 95% and most preferably 99% identical or homologous to the polypeptide sequence (SEQ. ID 57).

In some embodiments, other antibacterial proteins can be advantageously delivered using the inventive hydrogels, for instance endolysins, phage proteins, phage enzymatic formulations, and combinations thereof. Such proteins are often designated bacteriolytic enzymes. Bacteriolytic enzymes with activity against either gram-negative or gram-positive bacteria (or both) may be included in the inventive hydrogels. Exemplary enzymes include lytic enzymes such as lysozyme (muramidase or N-acetylmuramide glucanhydrolase)

In some embodiments, the hydrogels disclosed herein can include one or more bone morphogenetic proteins. As used herein, bone morphogenetic protein (i.e., BMP) includes wild-type proteins and variants thereof, active fragments of such wild-type and variants, or synthetic peptide mimetics thereof. A variety of osteogenic bone morphogenic proteins are known and can be used in embodiments herein either alone or in combinations of bone morphogenic proteins. The bone morphogenic protein can be or include any bone morphogenic protein, for instance: BMP-2, BMP-4, BMP-5, BMP-6, BMP-7, and/or BMP-9, preferably BMP-2. Recombinant human bone morphogenetic proteins (rhBMPs) can also be employed. Most preferably, the bone morphogenetic protein is rhBMP-2, rhBMP-4, or a heterodimer thereof. rhBMP-2 and rhBMP-7 are commercially available and such commercial forms can be used herein.

The synthetic hydrogels include a network of crosslinked hydrophilic polymer conjugated to adhesion peptides. Suitable hydrophilic polymers include polyalkylene glycol polymers, polyalkylene oxide homopolymers such as polypropylene glycols, polyoxyethylenated polyols, copolymers thereof and block copolymers thereof, as well as poly(oxyethylated polyol), poly(olefinic alcohol), poly(vinylpyrrolidone), poly(hydroxypropylmethacrylamide), poly(α-hydroxy acid), poly(vinyl alcohol), polyphosphazene, polyoxazoline, poly(N-acryloylmorpholine) and copolymers, terpolymers, and mixtures thereof. The molecular weight of the hydrophilic polymer can be from 1,000-1,000,000, from 1,000-500,000, from 1,000-250,000, from 1,000-150,000, from 1,000-100,000, from 1,000-50,000, from 5,000-100,000, from 5,000-50,000, from 10,000-100,000, from 10,000-50,000, from 20,000-100,000, from 20,000-80,000, from 20,000-60,000, from 20,000-40,000, or from 40,000-60,000.

In certain embodiments, the crosslinked hydrophilic polymer is a polyethylene glycol, i.e., PEG. The PEG can have a molecular weight from 1,000-1,000,000, from 1,000-500,000, from 1,000-250,000, from 1,000-150,000, from 1,000-100,000, from 1,000-50,000, from 5,000-100,000, from 5,000-50,000, from 10,000-100,000, from 10,000-50,000, from 20,000-100,000, from 20,000-80,000, from 20,000-60,000, from 20,000-40,000, or from 40,000-60,000.

In preferred embodiments, the crosslinked hydrophilic polymer is a branched or multi-arm polymer. As used herein, a multi-arm polymer describes a polymer having a central core with at least two polymers covalently attached thereto. Multi-arm polymers can have 2, 3, 4, 5, 6, 7, 8 or more polymer arms. Preferred multi-arm polymers, as defined above, include those with 4 arms. Generally, all of the polymers attached to the core are the same, but in some instances different hydrophilic polymers, as defined above, can be used. Suitable cores include those derived from polyols, including glycerol (3-arm), pentaerythritol (4-arm), tetraglycerol (6-arm), and hexaglycerol (8-arm). A particularly preferred polymer is a 4-arm PEG, having a total molecular weight from 1,000-1,000,000, from 1,000-500,000, from 1,000-250,000, from 1,000-150,000, from 1,000-100,000, from 1,000-50,000, from 5,000-100,000, from 5,000-50,000, from 10,000-100,000, from 10,000-50,000, from 20,000-100,000, from 20,000-80,000, from 20,000-60,000, from 20,000-40,000, or from 40,000-60,000.

In certain embodiments, the crosslinked hydrophilic polymer network can have the general formula:

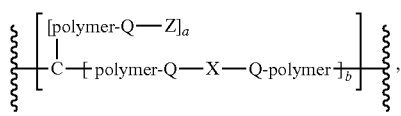

wherein 'polymer' in each case independently represents any hydrophilic polymer, including those defined above, C represents a core, Q represents a linker, Z represents an adhesion peptide, X represents a crosslinker, a is greater than 0, and b is greater than 1. In some embodiments, the sum a+b is no greater than 3, no greater than 4, no greater than 5, no greater than 6, no greater than 7, no greater than 8, no greater than 9, or no greater than 10. In other embodiments, the sum a+b is at least 3, at least 4, at least 5, no at least 6, at least 7, at least 8, at least 9, or at least 10.

In some embodiments, the hydrophilic polymer can be a poly(ethylene glycol), i.e., networks having the formula:

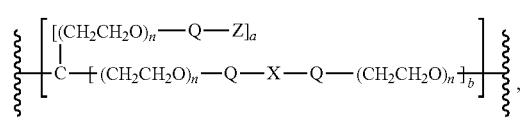

wherein C represents a core, n is an integer from 20-2,000, Q is a linking moiety, Z is an adhesion peptide, X is a crosslinker, a is greater than 0 and b is greater than 1. In some embodiments, the sum a+b is no greater than 3, no greater than 4, no greater than 5, no greater than 6, no greater than 7, no greater than 8, no greater than 9, or no greater than 10. In other embodiments, the sum a+b is at least 3, at least 4, at least 5, no at least 6, at least 7, at least 8, at least 9, or at least 10.

Suitable C groups can be derived from a polyol such as glycerol, pentaerythritol, sorbitol, mannitol, tetraglycerol, and hexaglycerol. In some instances, the core can have the general structure:

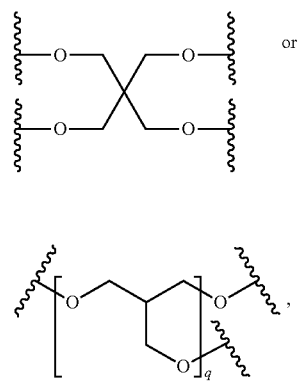

wherein q is any integer, for instance 1, 2, 3, 4, 5, 6, 7, 8, 9, or 10 and represents a link to a hydrophilic polymer, as described above. Other suitable polyols include carbohydrates, including monosaccharides and di-saccharides, such as glucose, xylose, mannose, galactose, sucrose, maltose, trehalose and fructose, and cyclic polyols like cyclopropane-1,2,3-triol, cyclobutane-1,2,3,4-tetraol, cyclopentane-1,2,3,4-tetraol, cyclopentane-1,2,3,4,5-pentaol, cyclohexane-1,2,4,5-tetraol, cyclohexane-1,2,3,4,5,6-hexaol, and the like.

Suitable Q group include those formed via Michael addition between a nucleophilic group on the adhesion peptide or crosslinker, and a Michael acceptor bonded to the hydrophilic polymer. For instance, in some embodiments, Q represents a group having the formula:

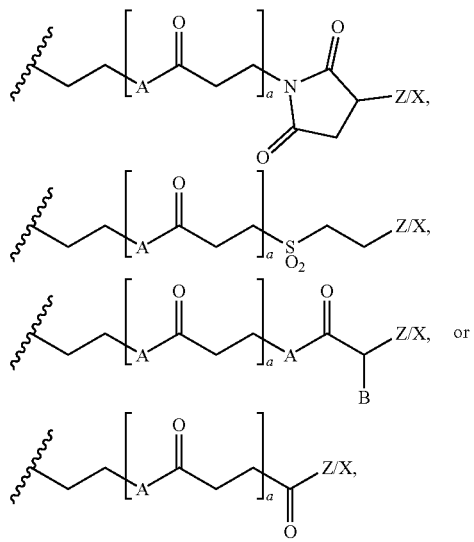

wherein A is independently selected from O or NH, a is independently selected from 0 or 1, B is selected from hydrogen or methyl, Z/X in each case independently represents either an adhesion peptide or crosslinker, and represents a link to a hydrophilic polymer, as described above.

In some embodiments, the adhesion peptide can include the sequence RGD. In some embodiments, the adhesion peptide can include GRGDSPC (SEQ. ID 1), CRGDS(SEQ. ID 2), CRGDSP (SEQ. ID 3), CPHSRN (SEQ. ID 4), CGWGGRGDSP (SEQ. ID 5), CGGSIDQVEPYSSTAQ (SEQ. ID 6), CGGRNIAEIIKDI (SEQ. ID 7), CGGDITYVRLKF (SEQ. ID 8), CGGDITVTLNRL (SEQ. ID 9), CGGRYVVLPR (SEQ. ID 10), CGGKAFDITYVRLKF (SEQ. ID 11), CGGEGYGEGYIGSR (SEQ. ID 12), CGGATLQLQEGRLHFXFDLGKGR, wherein X=Nle (SEQ. ID 13), CGGSYWYRIEASRTG (SEQ. ID 14), CGGGEFYFDLRLKGDKY (SEQ. ID 15), CKGGNGEPRGDTYRAY (SEQ. ID 16), CKGGPQVTRGDVFTMP (SEQ. ID 17), CGGNRWHSIYITRFG (SEQ. ID 18), CGGASIKVAVSADR (SEQ. ID 19), CGGTTVKYIFR (SEQ. ID 20), CGGSIKIRGTYS (SEQ. ID 21), CGGSINNNR (SEQ. ID 22), CGGSDPGYIGSR (SEQ. ID 23), CYIGSR (SEQ. ID 24), CGGTPGPQGIAGQGVV (SEQ. ID 25), CGGTPGPQGIAGQRVV (SEQ. ID 26), CGGMNYYSNS (SEQ. ID 27), CGGKKQRFRHRNRKG (SEQ. ID 28), CRGDGGGGGGGGGGGGPHSRN (SEQ. ID 29), CPHSRNSGSGSGSGSGRGD (SEQ. ID 30), Acetylated-GCYGRGDSPG (SEQ. ID 31), ((GPP)SGPC) (SEQ. ID 32), CRDGS (SEQ. ID 33), cyclic RGD{Fd}C (SEQ. ID 34), CGGRKRLQVQLSIRT (SEQ. ID 35), CIKVAV (SEQ. ID 36), CGGAASIKVAVSADR (SEQ. ID 37), CGGKRTGQYKL (SEQ. ID 38), CGGTYRSRKY (SEQ. ID 39), CGGYGGGP(GPP)SGFOGERPP(GPP)4GPC (SEQ. ID 40), CGGKRTGQYKLGSKTGPGQK (SEQ. ID 41), QAKHKQRKRLKSSC (SEQ. ID 42), SPKHHSQRARKKKNKNC (SEQ. ID 43), CGGXBBXBX, wherein B=basic residue and X=hydropathic residue (SEQ. ID 44), and CGGXBBBXXBX, wherein B=basic residue and X=hydropathic residue (SEQ. ID 45). In some preferred embodiments, the adhesion peptide includes the sequence GRGDSPC (SEQ. ID 1). In some instances, the hydrogel can include two or more different adhesions peptides.

Suitable crosslinkers include enzymatically cleavable and non-cleavable peptide sequences. The peptide sequences will generally include a cysteine residue at each end of the sequence. Exemplary cleavable peptides include those that are cleavable by MMP, cathepsin, or other protease. Although the cysteine may be the final amino acid residue at each end of sequence, it is more preferable that the cross-linking peptides are terminated with a glycine or other inert residue. In some embodiments, the enzymatically cleavable peptide will include the dipeptide A-V, N-V, K-V, or Cit-V, in which Cit refers to citrulline. In other embodiments, the crosslinking peptides can include the sequences GCRDGPQG↓IWGQDRCG (SEQ. ID 46), GCRDGPQG↓TAGQDRCG (SEQ. ID 47), GCRDVPMS↓MRGGDRCG (SEQ. ID 48), GCRDIPVS↓LRSGDRCG (SEQ. ID 49), GCRDRPFS↓MIMGDRCG (SEQ. ID 50), GCRDVPLS↓LTMGDRCG (SEQ. ID 51), GCRDVPLS↓LYSGDRCG (SEQ. ID 52), GCRDIPES↓LRAGDRCG (SEQ. ID 53), GCRDSGESPAY↓NTADRCG (SEQ. ID 54), GCRDGGYAE↓LRMGGDRCG (SEQ. ID 55), GCRDGGPLG↓LYAGGDRCG (SEQ. ID 56), GCRDGPLG↓LWARDRCG (SEQ. ID 57), wherein ↓ represents a cleavable amide bond. In some embodiments, the crosslinker is a not a peptide, for instance a di-mercapto compound such as a 1,4-dithiothreitol (1,4-dimercapto-2,3-butanediol) or poly(ethylene glycol) dithiol. In some cases, the hydrogel can include two or more cleavable crosslinkers.

The compositions can include water in an amount of at least 70% by weight relative to the total weight of the composition. In some embodiments, the water can be present in an amount of at least 75%, at least 80%, at least 85%, at least 87.5%, at least 90%, at least 92.5%, or at least 95% by weight relative to the total weight of the composition. In some embodiments, the compositions will include the hydrophilic crosslinked polymer network in an amount no greater than 30%, no greater than 25%, no greater than 20%, no greater than 15%, no greater than 12.5%, no greater than 10%, no greater than 7.5%, or no greater than 5%, by weight relative to the total volume of the hydrogel. In certain embodiments, the crosslinked hydrophilic polymer network is present in an amount from 1-8%, from 2-7%, from 2-6%, from 3-6%, from 3-5%, or from 3.5-4.5% polymer weight by total volume of the composition. In certain embodiments, the crosslinked hydrophilic polymer network is present in an amount of about 4% polymer weight by total volume of the composition.

Lysostaphin may be present in the hydrogel in a variety of concentrations. For instance, the lysostaphin may be present in a concentration of at least 10 U/mL, at least 25 U/mL, at least 50 U/mL, at least 100 U/mL, at least 150 U/mL, at least 200 U/mL, at least 250 U/mL, at least 300 U/mL, at least 350 U/mL, at least 400 U/mL, at least 450 U/mL, at least 500 U/mL, at least 550 U/mL, at least 600 U/mL, at least 650 U/mL, at least 700 U/mL, at least 750 U/mL, at least 800 U/mL, at least 850 U/mL, at least 900 U/mL, at least 950 U/mL, or at least 1,000 U/mL. In some embodiments, the lysostaphin is present in a concentration from 10-1,000 U/mL, from 50-1,000 U/mL, from 100-1,000 U/mL, from 200-1,000 U/mL, from 300-1,000 U/mL, from 400-1,000 U/mL, from 500-1,000 U/mL, from 50-750 U/mL, from 150-750 U/mL, or from 250-750 U/mL.

Bone morphogenetic protein, especially BMP-2, may be present in the hydrogel in a variety of concentrations. For instance, the bone morphogenetic protein may be present in a concentration of at least 10 ng/mL, at least 25 ng/mL, at least 50 ng/mL, at least 75 ng/mL, at least 100 ng/mL, at least 150 ng/mL, at least 200 ng/mL, at least 250 ng/mL, at least 300 ng/mL, at least 350 ng/mL, at least 400 ng/mL, at least 450 ng/mL, or at least 500 ng/mL. In some embodiments, the bone morphogenetic protein may be present in a concentration from 10-500 ng/mL, from 25-500 ng/mL, from 50-500 ng/mL, from 75-500 ng/mL, from 100-500 ng/mL, from 150-500 ng/mL, from 200-500 ng/mL, from 250-500 ng/mL, from 50-250 ng/mL, or from 150-250 ng/mL.

The crosslinked networks disclosed herein may be prepared by first conjugating an adhesion peptide to a hydrophilic polymer having the formula:

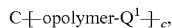

wherein C and "polymer" are as defined above, c is an integer greater than or equal to 3, and $Q^1$ is an electrophilic group capable of reacting with a thiol group. In some embodiments, the hydrophilic polymer is PEG, i.e., a compound of formula:

wherein C, n, c, and $Q^1$ are as defined above. In some embodiments, $Q^1$ represents a group having the formula:

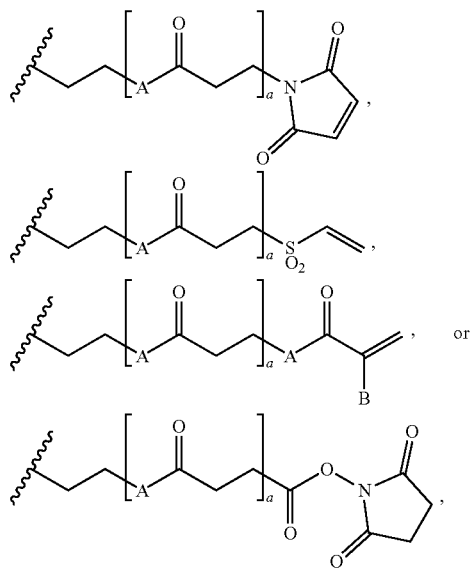

wherein A is independently selected from O or NH, a is independently selected from 0 or 1, B is selected from hydrogen or methyl, and ⸾ represents a link to a hydrophilic polymer, as described above.

The adhesion peptide can contain a single cysteine residue or thiol group, and will be combined such that there is a molar excess of $Q^1$ groups relative to cysteine/thiol groups in the adhesion peptide. For instance, molar ratio of $Q^1$ groups to cysteine/thiol residues can be from 10:1 to 1.5:1, from 8:1 to 1.5:1, from 6:1 to 1.5:1, from 4:1 to 1.5:1, from 3:1 to 1.5:1, from 2.5:1 to 1.5:1, from 5:1 to 2:1, from 5:1 to 3:1, or from 5:1 to 4:1. The molar ratio of nucleophilic groups in the crosslinker to unreacted $Q^1$ groups (assuming complete reaction with adhesion peptide) can be 1:1, greater than 1:1, e.g., 1.1:1, 1.2:1, or 1.5:1, less than 1:1, e.g., 0.9:1, 0.8:1, or 0.5:1, from 0.5:1 to 1.5:1, from 0.75:1 to 1.25:1, from 0.5:1 to less than 1:1, or from 1.5:1 to greater than 1:1.

Each of the hydrophilic polymer, adhesion peptide, crosslinker, lysostaphin, and bone morphogenetic protein can be separately combined with an appropriate aqueous solution, generally buffered to a pH from 5.0-8.0, from 5.0-7.0, from 5.0-6.5, from 5.0-6.0, from 5.5-6.0, from 5.5-6.5, from 6.5-7.5, from 7.2-7.6, or from 7.3-7.5. Any physiologically compatible buffer may be used, such as 4-(2-hydroxyethyl) piperazine-1-ethanesulfonic acid (HEPES), phosphate buffers, carbonate buffers, tromethamine (tris) buffers, including those formed with EDTA and an acid such as acetic acid, boric acid, and the like.

The relative ratios of the components may be as follows:

| Hydrogel component | Volume fraction of hydrogel component | Concentration factor of hydrogel component |
|---|---|---|
| Hydrophilic polymer | 0.3-0.5 | 2.5× |
| Adhesion peptide | 0.15-0.25 | 5× |
| Crosslinker | 0.15-0.25 | 5× |

The hydrophilic polymer may be combined with a solution of adhesive peptide such that the final adhesive peptide concentration is from 0.1-100 mM, from 0.5-75 mM, from 1-50 mM, from 5-25 mM, or from 7.5-15 mM, based on the total volume of the hydrogel. The mixture can be incubated at a temperature from 23-50° C., from 28-45° C., from 32-40° C., or at 37° C. for at least 5 minutes, at least 10 minutes, at least 15 minutes, or at least 20 minutes. The resulting product is designated the hydrogel precursor, which has the following structure:

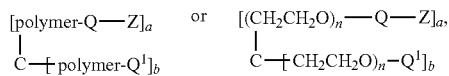

wherein C, 'polymer,' n, Q, $Q^1$, Z, a, and b have the meanings given above. The hydrogel precursor may be directly converted to a hydrogel by combination with the crosslinker, or may first be combined with lysostaphin and/or bone morphogenetic protein and subsequently combined with the crosslinker to form the hydrogel.

The compositions disclosed herein may be used to promote wound healing and tissue repair, especially for injured or diseased bone tissue. Injured bone tissue include bone fractures, such as stress fractures, greenstick fractures, buckle fractures, growth plate fractures, comminuted fractures, avulsion fracture, compression fracture, hairline fracture, impacted fracture, intraarticular fracture, spiral fracture, transverse fractures, oblique fractures, and pathologic fractures. In addition to the lysostaphin and/or bone morphogenetic protein, the hydrogel composition may further include additional therapeutics to facilitate healing and prevent infection. Suitable additional therapeutics include additional growth factors, additional antibiotics, antivirals, analgesics, cytokines, enzymes, aptamers, nucleic acids, and combinations thereof.

In some instances, a preformed hydrogel composition may be directly contacted with the site of tissue injury. In other instances, the composition may be administered subcutaneously adjacent or proximate to the injury. In some embodiment the hydrogel precursor is combined with the crosslinker at the site of injury at the time of administration. In such embodiments, the lysostaphin and/or bone morphogenetic protein may be first combined with either of the hydrogel precursor or crosslinker. A preferred method includes an in vivo hydrogel formation. The hydrogel precursor is loaded into a dispensing means, for instance a syringe, which is in fluid communication with a needle by way of a tube. Inside the tube is loaded the crosslinker, such that when the hydrogel precursor is expelled from the syringe, it combines with the crosslinker solution and is ejected from the needle into the directed site. The active agents, i.e., antibacterial protein and/or bone morphogenetic protein, may be combined with either the hydrogel precursor, crosslinker, or both.

Management of bone injuries and disease may require the use of an internal fixation device, such as, Kirschner wires (K-wires), pins, intramedullary rods or nails, cerclage wire, plates, wraps, and screws to stabilize bone fragments. These fixation devices may be loaded, coated, or otherwise impregnated with the hydrogel compositions described herein. In some embodiment, the fixation device will include one or more hollow chambers having one or more openings. The hydrogel can be loaded in the chamber, wherein it or constituent parts will gradually exit the chamber.

The hydrogels disclosed herein may also be used in the context of a bone graft. The hydrogel may be loaded or formed inside a wrap or sleeve, which is then placed over or around the damage tissue. In cases in which a segment of bone is completely removed, either due to severe injury or disease, the sleeve may be used to join the severed ends of the bone, with the hydrogel contained within the sleeve. Over time, bone tissue is regenerated within the sleeve, ultimately connecting the severed ends. The sleeve may be shaped to correspond to the outer surface of the missing bone fragment. The sleeve may further contain one or more openings, for instance holes or slots.

EXAMPLES

The following examples are for the purpose of illustration of the invention only and are not intended to limit the scope of the present invention in any manner whatsoever.

*S. aureus* strains UAMS-1 (ATCC 49230) and Xen29 (Perkin-Elmer) were grown at 37° C. on TSA or Luria-Burtani (LB) agar supplemented with 50 µg/mL kanamycin, respectively.

Example 1: Lysostaphin and BMP-2 Co-Delivering Hydrogel Synthesis

Hydrogels were synthesized using 4-arm 20 kDa poly(ethylene glycol)-maleimide (PEG-4MAL) macromer (Lysan Bio) functionalized with the collagen-mimetic peptide GGYGGP(GPP)5GFOGER(GPP)5GPC (GFOGER) (New England Peptide) (SEQ ID. 59), lysostaphin (AMBI), *S. aureus* UAMS-1 or Xen29, and then cross-linked using the cysteine-flanked protease degradable peptide GCRDVPMSMRGGDRCG (VPM) (SEQ ID. 48). All components were suspended in 100 mM MES buffered PBS at a pH of 5.5-6.0. Single colonies of UAMS-1 or Xen29 were picked from agar plates and suspended in PBS to an optical density of 0.20 measured at 600 nm using a benchtop spectrophotometer (Microscan Turbidity Meter, Siemens). The bacteria suspension was diluted 100-fold for UAMS-1 studies and 10 fold for Xen29 studies. BMP-2 (R&D Systems) was prepared at 333 ng/mL in 4 mM HCl. For hydrogels with lysostaphin, the enzyme was added to PEG-MAL. Hydrogels were synthesized by mixing 4:2:2:1:1 parts PEG-4MAL, GFOGER, VPM, BMP-2, and bacteria, followed by injection into a polyimide tube with 300 µm laser machined holes (Microlumen). The final hydrogel composition was 4.0% w/v 20 kDa PEG-4MAL, 1.0 mM GFOGER, 412±85 CFU/gel UAMS-1, 100 ng BMP-2, with or without 1 U lysostaphin. Hydrogels were polymerized at 37° C. and 5% CO2 for 15 minutes and then swollen in PBS cut into 4 mm segments, and kept in PBS until implantation.

Example 2: Murine Radial Segmental Defect Infection Model

All live animal experiments were performed in accordance with the Institutional Animal Care and Use Committee at Georgia Institute of Technology under veterinary supervision. Male 10-12 weeks old C57/B6 mice (Jackson Laboratories) were anesthetized via isoflurane inhalation. Depilatory cream was used to remove fur from the right forelimb. The limb was surface disinfected by applying 70% isopropyl alcohol followed by chlorohexidine solution. 1 mg/kg slow release buprenorphine was injected intraperitoneally before surgery as an analgesic. A 1 cm incision was made on the right forelimb over the radius, followed by blunt dissection of the radius. A 2.5 mm section of the radius was then excised using a custom-made double-bladed bone cutting device. A 4 mm polyimide implant tube containing the hydrogel was then fitted over each end of the radius. For mice receiving local gentamicin therapy, infected UAMS-1 containing implants were dipped in 10 mg/mL gentamicin followed by dipping in 0.9% w/v sodium chloride prior to implantation. The wound was sutured closed and an X-ray image (MX-20 Radiography System, Faxitron) was taken of the radius to confirm appropriate implant placement. Mice placed under warming lamp and monitored until ambulatory.

Example 3: Recovery of Bacteria from Tissue Samples

Mice were euthanized via $CO_2$ inhalation and the right forelimb was sterilized with 70% isopropyl alcohol and the skin was removed. The implant tube, surrounding tissue and bone were removed, weighed, and kept on ice. Tissue samples from the mouse forelimb were homogenized using bead beating tubes (1.4 mm zirconium beads, OPS Diagnostics) in combination with the FastPrep 24 (MP Biomedicals) set to 6 m/s for a total of 5 successive runs, 40 s in duration. Liver samples were homogenized for 10 sec using a Lab Gen 7 (Cole Palmer) tissue homogenizer in 12×75 mm sterile tubes. Single cell bacterial suspensions were then prepared by a series of sonication and vortexing steps (10 min sonication, 30 sec vortex, 5 min sonication, 30 sec vortex, 30 sec sonication, 30 sec vortex). These single cell suspensions were then serially diluted in PBS, plated on agar plates, incubated overnight at 37° C., and enumerated. Bacterial counts were normalized to tissue weight and reported as CFU/mg or CFU/implant if tissue weights were not recorded.

Microcomputed Tomography and Bone Volume Quantification

Animals were anesthetized via isoflurane inhalation and a 3.2 mm length sectioned centered over the radial defect was imaged using a VivaCT system (Scano Medical) with the following imaging parameters: 145 µA intensity, 55 kVp energy, 200 ms integration time, and 15 µm resolution. Contours of the radius within the implant tube were drawn on each 2D section and a Gaussian filter was applied (sigma=1, support=1, threshold=540 mg HA/ccm) to quantify bone volume.

Mechanical Testing of Radii

Briefly, mice were euthanized via $CO_2$ inhalation and the right forelimb was dissected, wrapped in saline soaked gauze, and frozen at −20° C. until the time of analysis.

Samples were thawed under running deionized water, and the radius and ulna and surrounding tissue was removed from the forelimb. The ulna was then cut at its midpoint using a scalpel blade to ensure the mechanical integrity of the radius was evaluated. Samples were potted in woods metal containing blocks. Torsion to failure testing was performed using a Bose Electroforce ELF 3200 system in conjunction with a 0.07 N·m torque sensor (Transducer Techniques) by applying a constant rotation of 3 degree per second. The maximum recorded torque value was reported.

Dot Blot for Anti-Lysostaphin Antibody Generation

Pre-exposure blood samples were collected at the time of surgery via cheek bleed. Post-exposure blood samples were collected 4 weeks after surgery by cardiac puncture after $CO_2$ euthanasia. Blood samples were clotted, centrifuged, and serum was collected and stored at −80° C. until analysis. The dot blot assay was performed using a vacuum driven Manifold I Spot Blot System (Schleicher & Schuell). The nitrocellulose membrane was coated with lysostaphin (AMBI, 100 μg/mL), blocked, washed, and then 10,000 fold diluted serum samples were exposed to the membrane. A mouse anti-lysostaphin polyclonal IgG (Antibody Research Corporation) was used as a positive control. Anti-lyso-staphin antibodies were detected using an AlexaFluor 488-conjugated polyclonal goat anti-mouse IgG antibody (Abcam). A Typhoon FLA 9500 gel imager (GE Healthcare) was used to image the membrane. ImageQuant (GE Healthcare) was used to quantify blot intensity. Positive results were determined to be five times the average intensity of serum samples from animals that were not exposed to lysostaphin.

Liver Function Analysis

Mice were euthanized by $CO_2$ inhalation and blood was taken via cardiac puncture. Serum was separated and samples were sent for blood chemistry testing at Antech Diagnostics.

Histology of Tissue Samples

Mice were euthanized via $CO_2$ asphyxiation and the right forelimb was dissected, fixed in 10% neutral buffered formalin, and decalcified in formic acid. Sampled were then processed and embedding in paraffin. Sections (5 μm) of the radius and implant tube were cut, and stained with either hematoxylin and eosin, safranin-O and fast green, or gram stain using standard methods. Color images of the tissue sections were taken with a Nikon Eclipse E600 microscope using a Plan Fluor 20× objective (Nikon), Micropublisher 5.0 RTV (Q imaging) color camera, and Q-Capture software (Q imaging).

In Vivo Flow Cytometry Analysis

Mice were euthanized via $CO_2$ asphyxiation and the right forelimb was dissected. The implant tube and surrounding tissue were removed, weighed, and digested in collagenase type 1-A (1 mg/mL, Sigma) at 37° C. for 45 min. Following digestion, samples were separated using a cell strainer to form a single cell suspension. The single cell suspensions were stained for flow cytometry using standard methods. The samples were analyzed on a FACS-Aria IIIu flow cytometer (BD Biosciences). The antibodies used for cell staining were: AlexaFluor 488 conjugated anti-CD206 (BioLegend), BV421 conjugated anti-CD19 (BioLegend), BV605 conjugated anti-CD4 (BioLegend), BV785 anti-CD8a (BioLegend), PE/Cy7 conjugated anti-CD3c (BioLegend), BV510 conjugated anti-Ly-6C (BioLegend), APC conjugated anti-F4/80 (BioLegend), APC/Cy7 conjugated anti-Ly-6G (BioLegend), and PE conjugated anti-CD86 (BioLegend). Live/dead staining was performed using the Zombie Red fixable viability kit per manufacturer's instructions (BioLegend). Precision Counting Beads (BioLegend) were used to report cell numbers.

In Vivo Cytokine Array Analysis

Following euthanasia via $CO_2$ inhalation, the right forelimb was dissected and the implant tube and surrounding tissue was removed for processing. The samples were placed in RIPA buffer, minced, and sonicated. The homogenate was centrifuged at 10,000 g for 5 minutes and the supernatant was filtered using a 0.45 μm spin filter, snap frozen in liquid nitrogen, and stored at −80° C. until the time of analysis. A MilliPlex 25-plex mouse cytokine array kit (Millipore Sigma) was used to quantify tissue concentrations of G-CSF, GM-CSF, IFN-γ, IL-1α, IL-1β, IL-2, IL-4, IL-5, IL-6, IL-7, IL-9, IL-10, IL-12p40, IL-12p70, IL-13, IL-15, IL-17, IP-10, KC, MCP-1, MIP-1α, MIP-1β, MIP-2, RANTES, and TNF-α per the manufacturer's instructions. Results were read using a Luminex system (Luminex Corporation) and normalized to total protein content of the sample measured with a bicinchoninic acid (BCA) assay kit (Pierce by ThermoFisher). Samples below or above the detection limit of the assay were reported as the minimum or maximum value respectively.

Statistics

All data is plotted as individual data points (biological replicates) with a line indicating the mean and the error bars representing the standard deviation of the mean. A P value less than 0.05 was deemed statistically significant. Statistical comparisons between two groups were made with the Student's t Test. Multivariate parametric data was analyzed using ANOVA with Tukey's post-hoc test and non-parametric data was analyzed using the Kruskall-Wallis test with Dunn's multiple comparison test. A two-way ANOVA with a Bonferroni correction was used to identify statistically significant cytokines. A chi-square test was used to assess for differences in the frequency of anti-lysostaphin antibody generation. All calculations were performed using Prism (GraphPad). Hierarchal cluster analysis was performed on the cytokine data using JMP Pro 13.

| ANTIBODY | CLONE | FLUOR | TEST VOLUME (μL) | CATALOG # |
|---|---|---|---|---|
| CD206 | C068C2 | AF488 | 0.75 | 141709 |
| CD19 | 6D5 | BV421 | 1.575 | 115537 |
| CD4 | GK1.5 | BV605 | 1.5 | 100451 |
| CD8 | 53-6.7 | BV785 | 1.5 | 100749 |
| LY6C | HK1.4 | BV510 | 1.575 | 128033 |
| F480 | BM8 | APC | 1.575 | 123115 |
| CD3 | 145-2C11 | PE-Cy7 | 1.575 | 100319 |
| LY6G | 1A8 | APC-Cy7 | 1.5 | 127623 |
| CD11B | M1/70 | BV711 | 1.575 | 101241 |
| CD86 | GL-1 | PE | 1.5 | 105007 |
| Zombie Red™ Fixable Viability Kit | n/a | n/a | 1 | 423109 |

Immune cell profiling antibody characteristics. Details regarding flow cytometry antibody targets, clones, fluorophores, test volume used per sample, and BioLegend catalog number.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A composition comprising lysostaphin, dispersed in a hydrogel matrix, wherein the hydrogel matrix comprises a crosslinked hydrophilic polymer network covalently bonded to a plurality of adhesion peptides, wherein the crosslinked hydrophilic polymer network has the general formula:

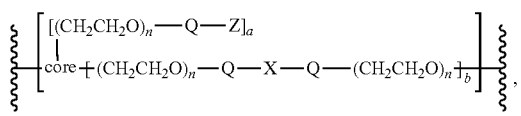

wherein core represents a core, n is an integer from 20-2,000, Q is a linking moiety, Z is an adhesion peptide, X is a crosslinker, a is greater than 0 and b is greater than 1, provided the sum of a+b does not exceed 7.

2. The composition according to claim 1, further comprising at least one bone morphogenetic protein.

3. The composition according to claim 1, wherein the composition comprises water in an amount of at least 80% by weight.

4. The composition according to claim 1, wherein core represents a group having the formula:

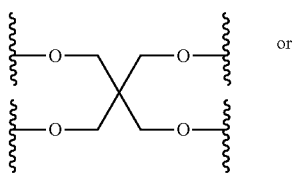 or

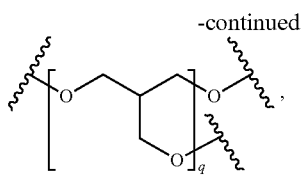

wherein q is from 1-6.

5. The composition according to claim 1, wherein Q represents a group having the formula:

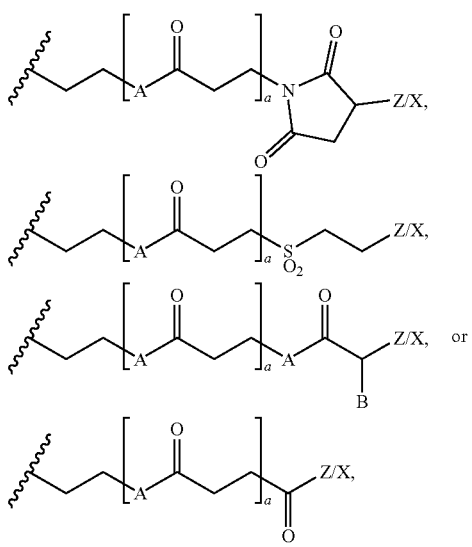

wherein A is independently selected from O or NH, a is independently selected from 0 or 1, B is selected from hydrogen or methyl, and Z/X in each case independently represents either an adhesion peptide or cross-linker.

6. The composition according to claim 1, wherein the adhesion peptide comprises the amino acid sequence RGD.

7. The composition according to claim 1, wherein the adhesion peptide comprises the sequence GRGDSPC (SEQ. ID 1), CRGDS (SEQ. ID 2), CRGDSP (SEQ. ID 3), CPHSRN (SEQ. ID 4), CGWGGRGDSP (SEQ. ID 5), CGGSIDQVEPYSSTAQ (SEQ. ID 6), CGGRNIAEIIKDI (SEQ. ID 7), CGGDITYVRLKF (SEQ. ID 8), CGGDITVTLNRL (SEQ. ID 9), CGGRYVVLPR (SEQ. ID 10), CGGKAFDITYVRLKF (SEQ. ID 11), CGGEGYGEGYIGSR (SEQ. ID 12), CGGATLQLQEGRLHFXFDLGKGR, wherein X=Nle (SEQ. ID 13), CGGSYWYRIEASRTG (SEQ. ID 14), CGGGEFYFDLRLKGDKY (SEQ. ID 15), CKGGNGEPRGDTYRAY (SEQ. ID 16), CKGGPQVTRGDVFTMP (SEQ. ID 17), CGGNRWHSIYITRFG (SEQ. ID 18), CGGASIKVAVSADR (SEQ. ID 19), CGGTTVKYIFR (SEQ. ID 20), CGGSIKIRGTYS (SEQ. ID 21), CGGSINNNR (SEQ. ID 22), CGGSDPGYIGSR (SEQ. ID 23), CYIGSR (SEQ. ID 24), CGGTPGPQGIAGQGVV (SEQ. ID 25), CGGTPGPQGIAGQRVV (SEQ. ID 26), CGGMNYYSNS (SEQ. ID 27), CGGKKQRFRHRNRKG (SEQ. ID 28), CRGDGGGGGGGGGGGGPHSRN (SEQ. ID 29), CPHSRNSGSGSGSGSGRGD (SEQ. ID 30), Acetylated-GCYGRGDSPG (SEQ. ID 31), ((GPP)5GPC) (SEQ. ID 32), CRDGS (SEQ. ID 33), cyclic RGD{Fd}C (SEQ. ID 34), CGGRKRLQVQLSIRT (SEQ. ID 35), CIKVAV (SEQ. ID 36), CGGAASIKVAVSADR (SEQ. ID 37), CGGKRTGQYKL (SEQ. ID 38), CGGTYRSRKY (SEQ. ID 39), CGGYGGGP(GPP)5GFOGERPP(GPP)4GPC (SEQ. ID 40), CGGKRTGQYKLGSKTGPGQK (SEQ. ID 41), QAKHKQRKRLKSSC (SEQ. ID 42), SPKHHSQRARKKKNKNC (SEQ. ID 43), CGGXBBXBX, wherein B=basic residue and X=hydropathic residue (SEQ. ID 44), CGGXBBBXXBX, wherein B=basic residue and X=hydropathic residue (SEQ. ID 45), GGYGGP(GPP)5GFOGER(GPP)5GPC (SEQ. ID 59), or a combination thereof.

8. The composition according to claim 1, wherein the adhesion peptide comprises the amino acid sequence GRGDSPC (SEQ. ID 1).

9. The composition according to claim 1, wherein X is an MMP- or cathepsin- or other protease-cleavable or non-cleavable peptide comprising at least two cysteine residues at each end of the sequence.

10. The composition according to claim 1, wherein X comprises a peptide having the sequence GCRDGPQG↓IWGQDRCG (SEQ. ID 46), GCRDGPQ-G↓IAGQDRCG (SEQ. ID 47), GCRDVPMS↓MRGGDRCG (SEQ. ID 48), GCRDIPVS↓LRSGDRCG (SEQ. ID 49), GCRDRPFS↓MIMGDRCG (SEQ. ID 50), GCRDVPLS↓LTMGDRCG (SEQ. ID 51), GCRDVPLS↓LYSGDRCG (SEQ. ID 52), GCRDIPES↓LRAGDRCG (SEQ. ID 53), GCRDSGESPAY↓NTADRCG (SEQ. ID 54), GCRDGGYAE↓LRMGGDRCG (SEQ. ID 55), GCRDGGPLG↓LYAGGDRCG (SEQ. ID 56), GCRDGPLG↓LWARDRCG (SEQ. ID 57), 1,4-dithiothreitol poly(ethylene glycol) dithiol, or a combination thereof.

11. A composition comprising lysostaphin, dispersed in a hydrogel matrix, wherein the hydrogel matrix is obtained by crosslinking a hydrophilic polymer conjugated to a plurality of adhesion peptides, wherein the hydrophilic polymer has the general formula:

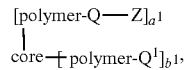

wherein 'polymer' represents a polyethylene glycol, core represents a core, Q represents a linker, Z represents an adhesion peptide, $Q^1$ represents a functional group capable of reacting with cysteine, and the sum of $a^1+b^1$ together is an integer of 3 or greater that does not exceed 7.

12. The composition according to claim 11, further comprising at least one bone morphogenetic protein.

13. A method of repairing a tissue injury, comprising contacting the injured tissue with the composition of claim 1.

14. The method according to claim 13, wherein the tissue injury comprises a bone fracture.

15. The method according to claim 13, wherein the tissue injury is a segmental bone injury, and the composition is disposed within a hollow sleeve.

* * * * *

UNITED STATES PATENT AND TRADEMARK OFFICE
CERTIFICATE OF CORRECTION

| | |
|---|---|
| PATENT NO. | : 11,565,024 B2 |
| APPLICATION NO. | : 16/191685 |
| DATED | : January 31, 2023 |
| INVENTOR(S) | : Andres J. Garcia and Christopher Thomas Johnson |

It is certified that error appears in the above-identified patent and that said Letters Patent is hereby corrected as shown below:

In the Claims

Claim 10, Column 44, Line 32 reading:
RAGDRCG (SEQ. ID 53), GCRDSGESPAY↓NTADRCG

Should read:
RAGDRCG (SEQ. ID 53), GCRDSGESPAY↓YTADRCG

Signed and Sealed this
Twenty-first Day of March, 2023

Katherine Kelly Vidal
Director of the United States Patent and Trademark Office